US012691118B2

(12) United States Patent
Li et al.

(10) Patent No.: US 12,691,118 B2
(45) Date of Patent: Jul. 28, 2026

(54) ALLOSTERIC AGONISTS AND POSITIVE ALLOSTERIC MODULATORS OF GLUCAGON-LIKE PEPTIDE 1 RECEPTOR

(71) Applicant: University of the Sciences, Philadelphia, PA (US)

(72) Inventors: Zhijun Li, Bala Cynwyd, PA (US); Tejashree Redij, Warrington, PA (US); James McKee, Havertown, PA (US); Zhiyu Li, Woodstock, MD (US); Jeffrey Campbell, Philadelphia, PA (US)

(73) Assignee: Saint Joseph's University, Philadelphia, PA (US)

( * ) Notice: Subject to any disclaimer, the term of this patent is extended or adjusted under 35 U.S.C. 154(b) by 1025 days.

(21) Appl. No.: 17/602,118

(22) PCT Filed: Apr. 10, 2020

(86) PCT No.: PCT/US2020/027604
§ 371 (c)(1),
(2) Date: Oct. 7, 2021

(87) PCT Pub. No.: WO2020/210582
PCT Pub. Date: Oct. 15, 2020

(65) Prior Publication Data

US 2022/0193080 A1 Jun. 23, 2022

Related U.S. Application Data

(60) Provisional application No. 62/832,766, filed on Apr. 11, 2019.

(51) Int. Cl.

| | |
|---|---|
| ***A61K 31/519*** | (2006.01) |
| ***A61K 31/155*** | (2006.01) |
| ***A61K 31/195*** | (2006.01) |
| ***A61K 31/381*** | (2006.01) |
| ***A61K 31/425*** | (2006.01) |
| ***A61K 31/426*** | (2006.01) |
| ***A61K 31/64*** | (2006.01) |
| ***A61K 38/22*** | (2006.01) |
| ***A61P 3/10*** | (2006.01) |
| ***C07D 333/68*** | (2006.01) |
| ***C07D 495/04*** | (2006.01) |

(52) U.S. Cl.
CPC .......... *A61K 31/519* (2013.01); *A61K 31/155* (2013.01); *A61K 31/195* (2013.01); *A61K 31/381* (2013.01); *A61K 31/426* (2013.01); *A61K 31/64* (2013.01); *A61K 38/22* (2013.01); *A61P 3/10* (2018.01); *C07D 333/68* (2013.01); *C07D 495/04* (2013.01)

(58) Field of Classification Search
CPC .. A61K 31/519; A61K 31/155; A61K 31/195; A61K 31/381; A61K 31/426; A61K 31/64; A61K 38/22; A61K 31/425; A61P 3/10; C07D 333/68; C07D 495/04
See application file for complete search history.

(56) References Cited

U.S. PATENT DOCUMENTS

| | | | | |
|---|---|---|---|---|
| 9,839,664 | B2 | 12/2017 | Boehm et al. | |
| 11,492,347 | B2 * | 11/2022 | Meldrum | C07D 403/12 |
| 12,018,021 | B2 * | 6/2024 | Chovatia | C07D 409/14 |
| 2007/0275962 | A1 * | 11/2007 | Koul | C07D 493/04 514/408 |
| 2009/0018149 | A1 * | 1/2009 | Missio | A61P 31/06 435/7.1 |

FOREIGN PATENT DOCUMENTS

WO 2013090454 A2 6/2013

OTHER PUBLICATIONS

Sanchez-Rangel E, Inzucchi SE. Metformin: clinical use in type 2 diabetes. Diabetologia. Sep. 2017;60(9):1586-1593. doi: 10.1007/s00125-017-4336-x. Epub Aug. 2, 2017. PMID: 28770321. (Year: 2017).*
Bluestone JA, Herold K, Eisenbarth G. Genetics, pathogenesis and clinical interventions in type 1 diabetes. Nature. Apr. 29, 2010; 464(7293):1293-300. doi: 10.1038/nature08933. PMID: 20432533; PMCID: PMC4959889. (Year: 2010).*
Malik et al. Is metformin poised for a second career as an antimicrobial? Diabetes Metab Res Rev 2018 34(4) e2975 (Year: 2018).*
Bennan-Krohn, Combination Antibiotic Testing, Am Soc Micro, 2018, https://asm.org/articles/2018/september/combination-antibiotic-testing-when-2-drugs-are-be (Year: 2018).*
Perrissin et al., European Journal Med Chem 1984, 19(5) pp. 420-424 (Year: 1984).*
CAS, RN 2090438-17-6, 2017 (Year: 2017).*
"PubChem 1082844", 2-[2-(4-Methylphenyl)-2-oxoethyl]sulfanyl-5,6,7,8-tetrahydro-3H-[1]-benzothiolo[2,3-d] pyrimidin-4-one, Jul. 10, 2005.

(Continued)

*Primary Examiner* — Bruck Kifle
*Assistant Examiner* — Kevin S Martin
(74) *Attorney, Agent, or Firm* — Saul Ewing LLP; Domingos J. Silva; Kevin T. O'Brien

(57) ABSTRACT

The present invention relates to the discovery of small molecule compounds that act as GLP-1R agonists and/or as positive allosteric modulators (PAMs) of GLP-1R. Such compounds are useful to treat, ameliorate, and/or prevent insulin resistance and/or diabetes in a mammal.

16 Claims, 13 Drawing Sheets

Specification includes a Sequence Listing.

(56) References Cited

OTHER PUBLICATIONS

"PubChem 13399857", Ethyl 2-amino-7-methyl-4,5,6,7-tetrahydro-1-benzothiophene-3-carboxylate, Feb. 8, 2007.
"VTv Therapeutics Reports Preclinical and Clinical Results on its Diabetes Candidate TTP273", Presented at Keystone Symposia on Molecular and Cellular Biology, accessed online https://ir.vtvtherapeutics.com/news-releases/news-release-details/vtv-therapeutics-reports-preclinical-and-clinical-results-its, Feb. 22, 2016, 2 pages.
"Zinc ID: ZINC01008161", 2-(5-{4-[(2-fluorobenzyl)oxy]benzylidene}-2,4-dioxo-1,3-thiazolidin-3-yl)-N-(4-methylphenyl)acetamide, Sep. 15, 2016.
"Zinc ID: ZINC02146229", 2-[(5-{[(4-chlorobenzyl)sulfanyl]methyl}-4-ethyl-4H-1,2,4-triazol-3-yl)sulfanyl]-N-(1,3-thiazol-2-yl)acetamide, Sep. 15, 2016.
"Zinc ID: ZINC08400241", 1-(3,4-dimethoxyphenyl)-6,7-dimethoxy-3-(4-methoxyphenyl)isoquinoline, Sep. 15, 2016.
Bueno , et al., "Positive Allosteric Modulation of the Glucagon-like Peptide-1 Receptor by Diverse Electrophiles", J Biological Chem, vol. 291, No. 20, May 13, 2016, pp. 10700-10715.
Jazayeri , et al., "Crystal structure of the GLP-1 receptor bound to a peptide agonist", Nature, vol. 546, Abstract Only, 2017, pp. 254-258.
Morris , et al., "Discovery of (S)-2-Cyclopentyl-N-((1-isopropylpyrrolidin2-yl)-9-methyl-1-oxo-2,9-dihydro-1H-pyrrido[3,4-b]indole-4-carboxamide (VU0453379): A Novel, CNS Penetrant Glucagon-Like Peptide 1 Receptor (GLP-1R) Positive Allosteric Modulator (PAM)", J Med Chem, vol. 57, 2014, pp. 10192-10197.
Redij , et al., "Discovery of allosteric small molecule anti-diabetic agent", University of the Sciences Research Day, Poster Presentation, Aug. 21, 2017, 1 page.
Redij , et al., "Rational design of anti-diabetic agent", 2017 American Society for Cell Biology (ASCB) Annual Meeting, Dec. 2-6, 2017, Philadelphia, PA, Poster Presentation, 2017, 1 page.
Redij , et al., "Rational design of anti-diabetic agents", University of the Sciences, Philadelphia, PA, Research Poster, Apr. 6, 2017, 1 page.
Redij , et al., "Structural Modeling and in Silico Screening of Potential Small-Molecule Allosteric Agonists of a Glucagon-Like Peptide 1 Receptor", ACS Omega, vol. 4, Jan. 11, 2019, pp. 961-970.
Wootten , et al., "Allostery and Biased Agonism at Class B G Protein-Coupled Receptors", Chem Rev, vol. 117, No. 1, Abstract Only, 2017, pp. 111-138.
International Search Report and Written Opinion dated Jul. 21, 2020 for corresponding PCT International Application PCT/US2020/027604.

* cited by examiner

1

2

3

4

5

6

7

8

ALLOSTERIC AGONISTS AND POSITIVE ALLOSTERIC MODULATORS OF GLUCAGON-LIKE PEPTIDE 1 RECEPTOR

CROSS-REFERENCE TO RELATED APPLICATIONS

This application is a 35 U.S.C. § 371 national phase application from, and claims priority to, International Application No. PCT/US2020/027604, filed Apr. 10, 2020, and published under PCT Article 21 (2) in English, which claims priority under 35 U.S.C. § 119(e) to U.S. Provisional Patent Application No. 62/832,766, filed Apr. 11, 2019, which are hereby incorporated herein by reference in their entireties.

STATEMENT REGARDING FEDERALLY SPONSORED RESEARCH OR DEVELOPMENT

This invention was made with government support under grant number UL1TR001878 awarded by the National Center for Advancing Translational Sciences of the National Institutes of Health. The government has certain rights in the invention.

SEQUENCE LISTING

The ASCII text file named 368763-7003WO1_Seq_Listing.txt created on Apr. 10, 2020, comprising 1 kilobyte, is hereby incorporated by reference in its entirety.

BACKGROUND OF THE INVENTION

Diabetes is a group of metabolic diseases characterized by hyperglycemia resulting from defects in insulin secretion, insulin action, or both. Insulin is a hormone produced by beta cells of the pancreatic islets and is responsible for regulating optimum level of blood glucose. The chronic hyperglycemia of diabetes is associated with long-term damage, dysfunction, and failure of different organs, especially the eyes, kidneys, nerves, heart, and blood vessels. In type 1 diabetes, body does not make insulin, and in type 2 diabetes body does not make or use insulin well.

The Glucagon-like peptide 1 receptor (GLP-1R) is a member of secretin-like class B family of G-protein coupled receptors (GPCRs) and plays an essential role in mediating the potentiation of insulin secretion. Hence, positive modulation of GLP-1R remains an effective strategy for the therapeutic treatment of type 2 diabetes.

Like other class B GPCRs, GLP-1R has an extracellular N-terminal domain and a seven transmembrane domain (7TM). In ligand binding, its N-terminal domain binds to C-terminal residues of the peptide hormone and its 7TM domain interacts with the N-terminal residues of the peptide for signaling. The large nature of the orthosteric binding site for GLP-1 hindered the development of orally active small molecule agonists of GLP-1R for therapeutic purpose. Another contributing factor is the lack of structural information on active state of the 7TM of GLP-1R until recently. Although high-throughput screenings have typically been used to identify small molecule GLP-1R agonists, further development of the lead compounds has not been successful. Up to now, no small molecule drugs acting as GLP-1R agonists are available in the market.

Thus, there is an unmet need in the art to develop small molecule drugs that target GLP-1R for the treatment of diabetes. The present invention addresses this unmet need.

BRIEF SUMMARY OF THE INVENTION

The present invention relates to compounds of Formula (I), or a salt, solvate, stereoisomer, geometric isomer, and/or tautomer thereof:

(I)

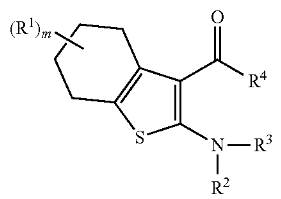

wherein m, $R^1$, $R^2$, $R^3$, and $R^4$ are defined elsewhere herein. The present invention further relates to pharmaceutical compositions comprising at least one pharmaceutically acceptable carrier and at least one compound contemplated herein, or a salt, solvate, stereoisomer, geometric isomer, and/or tautomer thereof. The present invention further relates to methods of treating, ameliorating, or preventing insulin resistance and/or diabetes in a subject. In certain embodiments, the method comprises administering to the subject a therapeutically effective amount of a compound contemplated herein, or a salt, solvate, stereoisomer, geometric isomer, and/or tautomer thereof.

BRIEF DESCRIPTION OF THE DRAWINGS

The following detailed description of certain embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 1A shows Compound Ia forming H-bonds (dotted lines) with residues S352 and N406. FIG. 1B shows the chemical structure of Compound Ia.

FIG. 5A shows the effect of GLP-1 in the presence (continuous line) and absence (dotted line) of Compound Ia (19.3 μM) on HEK293-CREB luciferase cells expressing WT GLP-1R (black) or mutant GLP-1R where N406 was mutated to A (grey). FIG. 5B shows the effect of GLP-1 in the presence (continuous line) and absence (dotted line) of Ia (19.3 μM) on HEK293-CREB luciferase cells expressing WT GLP-1R (black) or mutant GLP-1R where S352 was mutated to A (gray). FIG. 5C shows the effect of GLP-1 in the presence (continuous line) and absence (dotted line) of Compound Ia (19.3 μM) on HEK293-CREB luciferase cells expressing WT GLP-1R (black) or mutant GLP-1R where V332 is mutated to W. In all three curves, the effect of GLP-1 in the presence and absence of Compound Ia has been plotted as the luminescence fold change with respect to vehicle control (0.5% DMSO) and normalized to the respective protein concentrations. Data are average of three independent experiments with at least three technical replicates for each conditions and error bars for each concentration were plotted as SEM (n=3). Statistical analysis was done using 2-way ANOVA (**p<0.0001; p<0.001). The comparison is done between the data points of curves of luminescence caused due to GLP-1 alone and in combination with Compound Ia on WT GLP-1R or mutant GLP-1R.

FIG. 6A shows the effect of GLP-1 on HEK293 cells expressing human GLP-1R or empty vector in the presence or absence of Compound Ib (23.5 μM). FIG. 6B shows the effect of GLP-1 on HEK293 cells expressing human GLP-1R or empty vector in the presence or absence of Compound Ic (71 μM). GLP-1R activation was assessed as luminescence normalized to protein concentration and plotted as luminescence fold change with respect to vehicle control (0.5% DMSO). Data are average of three independent experiments with at least three technical replicates for each conditions and error bars for each concentration were plotted as SEM (n=3). Statistical analysis was done using 2-way ANOVA (**p<0.0001; p<0.001; *p<0.5). The comparison is done between the data points of the dose response curve generated due to GLP-1's effect on GLP-1R in the presence and absence of Compound Ib or Compound Ic.

FIG. 9A shows NNC0640 (NAM)-bound to GLP-1R (PDB ID: 5VEX). FIG. 9B shows PF-06372222 (NAM)-bound to GLP-1R (PDB ID: 5VEW). FIG. 9C shows a model of Compound 2 (ago-PAM)-bound to GLP-1R, generated by Glide SP docking using the cryo-EM structure of GLP-1R (PDB ID: 5VAI) and the proposed Compound 2 binding site in reference. FIG. 9D shows a model of Compound Ia (ago-PAM) bound to GLP-1R generated as reported herein.

DETAILED DESCRIPTION OF THE INVENTION

Figure 1B:
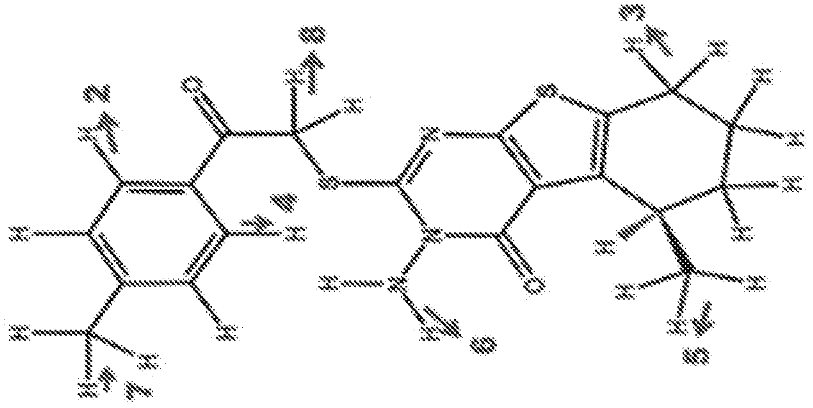
FIGS. 1A-1B depict docking pose in the predicted allosteric site of 7TM of GLP-1R (PDB ID: 5VAI) and chemical structure of small molecule agonist compound Ia (C-1; also known as 3-amino-5-methyl-2-((2-oxo-2-(p-tolyl)ethyl)thio)-5,6,7,8-tetrahydrobenzo[4,5]thieno[2,3-d]pyrimidin-4(3H)-one) of GLP-1R.

The present invention is related to discovery of Glucagon-like peptide 1 receptor (GLP-1R) agonists as well as the positive allosteric modulators (PAMs) of GLP-1R.

The GLP-1R is a well-established target for the treatment of type 2 diabetes and thus GLP-1R agonist-based therapies emerge as an effective approach to treat diabetes. However, development of nonpeptidic agonist drugs targeting GLP-1R has remained unsuccessful.

In the present invention, the information from the cryo-EM structure of GLP-1R in its active state was used to perform structure-based molecule design studies, including potential allosteric binding site prediction, in silico screening of drug-like compounds, site-specific mutagenesis studies, structure-based lead optimization, chemical syntheses, and in vitro assay validation. Collectively, these studies led to the identification of efficacious GLP-1R agonists or PAMs.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "ago-positive allosteric modulator" or "ago-PAM" as used herein refers to a compound that acts as both an allosteric agonist and a positive allosteric modulator of a receptor's response to a primary ligand. An allosteric agonist directly activates a receptor by binding to an allosteric agonist binding site, distinct from the primary (orthosteric) site. A positive allosteric modulator is an enhancer or a potentiator that induces an amplification of the effect of receptor's response to the primary ligand without directly activating the receptor.

A disease or disorder is "alleviated" if the severity of a symptom of the disease or disorder, the frequency with which such a symptom is experienced by a patient, or both, is reduced.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, pulmonary and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The terms "patient," "subject," or "individual" are used interchangeably herein, and refer to any animal, or cells thereof whether in vitro or in situ, amenable to the methods described herein. In a non-limiting embodiment, the patient, subject or individual is a human. As used herein, the term "pharmaceutically acceptable" refers to a material, such as a carrier or diluent, which does not abrogate the biological activity or properties of the compound, and is relatively non-toxic, i.e., the material can be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that can be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compounds prepared from pharmaceutically acceptable non-toxic acids or bases, including inorganic acids or bases, organic acids or bases, solvates, hydrates, or clathrates thereof. Pharmaceutically unacceptable salts may nonetheless possess properties such as high crystallinity, which have utility in the practice of the present invention, such as for example utility in process of synthesis, purification or formulation of compounds useful within the methods of the invention. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate).

Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, galacturonic acid, glycerophosphonic acids and saccharin (e.g., saccharinate, saccharate). Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the terms "pharmaceutically effective amount" and "effective amount" and "therapeutically effective amount" refer to a nontoxic but sufficient amount of an agent to provide the desired biological result. That result can be reduction and/or alleviation of the signs, symptoms, or causes of a disease, or any other desired alteration of a biological system. An appropriate therapeutic amount in any individual case can be determined by one of ordinary skill in the art using routine experimentation.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein and/or a symptom of a condition contemplated herein, with the purpose to cure, heal, alleviate, relieve, alter, remedy, ameliorate, improve, or affect a condition contemplated herein and/or the symptoms of a condition contemplated herein. Such treatments can be specifically tailored or modified, based on knowledge obtained from the field of pharmacogenomics.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "organic group" as used herein refers to any carbon-containing functional group. Examples can include an oxygen-containing group such as an alkoxy group, aryloxy group, aralkyloxy group, oxo (carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, $OC(O)N(R)_2$, CN, $CF_3$, $OCF_3$, R, C(O), methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, $C(O)N(R)_2$, $OC(O)N(R)_2$, $C(S)N(R)_2$, $(CH_2)_{0-2}N(R)C(O)R$, $(CH_2)_{0-2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R)_2$, C(O)N(OR)R, C(=NOR)R, and substituted or unsubstituted ($C_1$-$C_{100}$) hydrocarbyl, wherein R can be hydrogen (in examples that include other carbon atoms) or a carbon-based moiety, and wherein the carbon-based moiety can be substituted or unsubstituted.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, sec-butyl, tert-butyl, pentyl, sec-pentyl, isopentyl, neopentyl, hexyl, and cyclopropylmethyl. A non-limiting example is ($C_1$-$C_6$)alkyl, particularly methyl, ethyl, n-propyl, isopropyl, n-butyl, isobutyl, sec-butyl, t-butyl, n-pentyl, sec-pentyl, isopentyl, neopentyl, n-hexyl and cyclopropylmethyl.

As used herein, the term "alkenylene", employed alone or in combination with other terms, means, unless otherwise stated, a stable mono-unsaturated or di-unsaturated straight chain or branched chain hydrocarbon group having the stated number of carbon atoms wherein the group has two open valencies. Heteroalkenylene substituents can a group consisting of the stated number of carbon atoms and one or more heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkenyl group, including between the rest of the heteroalkenyl group and the fragment to which it is attached, as well as attached to the most distal carbon atom in the heteroalkenyl group.

As used herein, the term "alkynylene", employed alone or in combination with other terms, means, unless otherwise stated, a stable straight chain or branched chain hydrocarbon group with a triple carbon-carbon bond, having the stated number of carbon atoms wherein the group has two open valencies. Heteroalkynylene substituents can a group consisting of the stated number of carbon atoms and one or more heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkynyl group, including between the rest of the heteroalkynyl group and the fragment to which it is attached, as well as attached to the most distal carbon atom in the heteroalkynyl group.

As used herein, the term "substituted alkyl" means alkyl as defined above, substituted by one, two or three substituents selected from halogen, —OH, alkoxy, $—NH_2$, $—N(CH_3)_2$, —C(=O)OH, trifluoromethyl, —C≡N, —C(═O)O($C_1$-$C_4$)alkyl, —C(═O)$NH_2$, —$SO_2NH_2$, —C(═NH)$NH_2$, and —$NO_2$, preferably containing one or two substituents selected from halogen, —OH, alkoxy, —$NH_2$, trifluoromethyl, —N$(CH_3)_2$, and —C(═O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. A non-limiting example is ($C_1$-$C_3$)alkoxy, particularly ethoxy and methoxy.

The term "organic group" as used herein refers to any carbon-containing functional group. Examples can include an oxygen-containing group such as an alkoxy group, aryloxy group, aralkyloxy group, oxo (carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N$(R)_2$, CN, $CF_3$, $OCF_3$, R, C(O), methylenedioxy, ethylenedioxy, N$(R)_2$, SR, SOR, $SO_2R$, $SO_2N(R)_2$, $SO_3R$, C(O)R, C(O)C(O)R, C(O)$CH_2$C(O)R, C(S)R, C(O)OR, OC(O)R, C(O)N$(R)_2$, OC(O)N$(R)_2$, C(S)N$(R)_2$, $(CH_2)_{0-2}$N(R)C(O)R, $(CH_2)_{0-2}$N(R)N$(R)_2$, N(R)N(R)C(O)R, N(R)N(R)C(O)OR, N(R)N(R)CON$(R)_2$, N(R)$SO_2R$, N(R)$SO_2N(R)_2$, N(R)C(O)OR, N(R)C(O)R, N(R)C(S)R, N(R)C(O)N$(R)_2$, N(R)C(S)N$(R)_2$, N(COR)COR, N(OR)R, C(═NH)N$(R)_2$, C(O)N(OR)R, C(═NOR)R, and substituted or unsubstituted ($C_1$-$C_{100}$) hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N$(R)_2$, CN, NO, $NO_2$, $ONO_2$, azido, $CF_3$, $OCF_3$, R, O (oxo), S (thiono), C(O), S(O), methylenedioxy, ethylenedioxy, N$(R)_2$, SR, SOR, $SO_2R$, $SO_2N(R)_2$, $SO_3R$, C(O)R, C(O)C(O)R, C(O)$CH_2$C(O)R, C(S)R, C(O)OR, OC(O)R, C(O)N$(R)_2$, OC(O)N$(R)_2$, C(S)N$(R)_2$, $(CH_2)_{0-2}$N(R)C(O)R, $(CH_2)_{0-2}$N(R)N$(R)_2$, N(R)N(R)C(O)R, N(R)N(R)C(O)OR, N(R)N(R)CON$(R)_2$, N(R)$SO_2R$, N(R)$SO_2N(R)_2$, N(R)C(O)OR, N(R)C(O)R, N(R)C(S)R, N(R)C(O)N$(R)_2$, N(R)C(S)N$(R)_2$, N(COR)COR, N(OR)R, C(═NH)N$(R)_2$, C(O)N(OR)R, and C(═NOR)R, wherein R can be hydrogen or a carbon-based moiety; for example, R can be hydrogen, ($C_1$-$C_{100}$) hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH═CH($CH_3$), —CH═C$(CH_3)_2$, —C($CH_3$)═$CH_2$, —C($CH_3$)=CH($CH_3$), —C($CH_2CH_3$)═$CH_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C($CH_3$), —C≡C($CH_2CH_3$), —$CH_2$C≡CH, —$CH_2$C≡C($CH_3$), and —$CH_2$C≡C($CH_2CH_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl(2-thienyl, 3-thienyl), furyl(2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl(2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl(2-oxazolyl, 4-oxazolyl, 5-oxazolyl), thiazolyl(2-thiazolyl, 4-thiazolyl, 5-thiazolyl), pyridyl(2-pyridyl, 3-pyridyl, 4-pyridyl), pyrimidinyl(2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl(2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl(2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl(2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl(2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to $R—NH_2$, for example, alkylamines, arylamines, alkylarylamines; $R^2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form-$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The terms "epoxy-functional" or "epoxy-substituted" as used herein refers to a functional group in which an oxygen atom, the epoxy substituent, is directly attached to two adjacent carbon atoms of a carbon chain or ring system. Examples of epoxy-substituted functional groups include, but are not limited to, 2,3-epoxypropyl, 3,4-epoxybutyl, 4,5-epoxypentyl, 2,3-epoxypropoxy, epoxypropoxypropyl, 2-glycidoxyethyl, 3-glycidoxypropyl, 4-glycidoxybutyl, 2-(glycidoxycarbonyl)propyl, 3-(3,4-epoxycylohexyl)propyl, 2-(3,4-epoxycyclohexyl)ethyl, 2-(2,3-epoxycylopentyl)ethyl, 2-(4-methyl-3,4-epoxycyclohexyl)propyl, 2-(3,4-epoxy-3-methylcylohexyl)-2-methylethyl, and 5,6-epoxyhexyl.

As used herein, the term "optionally substituted" means that the referenced group can be substituted or unsubstituted. In certain embodiments, the referenced group is optionally substituted with zero substituents, i.e., the referenced group is unsubstituted. In other embodiments, the referenced group is optionally substituted with one or more additional group(s) individually and independently selected from groups described herein.

In certain embodiments, the substituents are independently selected from the group consisting of halogen, —$NH_2$, —OH, —$NH(CH_3)$, —$N(CH_3)_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, —C(═O)NH[substituted or unsubstituted alkyl, or substituted or unsubstituted phenyl], —C(═O)N[H or alkyl]$_2$, —OC(═O)N[substituted or unsubstituted alkyl]$_2$, —NHC(═O)NH[substituted or unsubstituted alkyl, or substituted or unsubstituted phenyl], —NHC(═O)alkyl, —N[substituted or unsubstituted alkyl]C(═O)[substituted or unsubstituted alkyl], —NHC(═O)[substituted or unsubstituted alkyl], —C(OH)[substituted or unsubstituted alkyl]$_2$, and —C($NH_2$)[substituted or unsubstituted alkyl]$_2$. In other embodiments, by way of example, an optional substituent is selected from oxo, fluorine, chlorine, bromine, iodine, —CN, —$NH_2$, —OH, —$NH(CH_3)$, —$N(CH_3)_2$, —$CH_3$, —$CH_2CH_3$, —$CH(CH_3)_2$, —$CF_3$, —$CH_2CF_3$, —$OCH_3$, —$OCH_2CH_3$, —$OCH(CH_3)_2$, —$OCF_3$, —$OCH_2CF_3$, —S(═O) 2-$CH_3$, —C(═O)$NH_2$, —C(═O)—$NHCH_3$, —NHC(═O)$NHCH_3$, —C(═O)$CH_3$, and —C(═O)OH. In yet one embodiment, the substituents are independently selected from the group consisting of $C_{1-6}$ alkyl, —OH, $C_{1-6}$ alkoxy, halo, amino, acetamido, oxo and nitro. In yet other embodiments, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain can be branched, straight or cyclic.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and Compositions

In one aspect, the invention provides a compound of Formula (I), or a or a salt, solvate, stereoisomer, geometric isomer, and/or tautomer thereof:

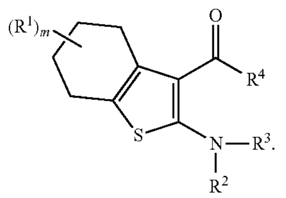

(I)

In various embodiments, each occurrence of $R^1$ is independently selected from the group consisting of hydrogen, F, Cl, Br, I, OR, $OC(O)N(R)_2$, CN, NO, $NO_2$, $ONO_2$, azido, $CF_3$, $OCF_3$, R, methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, $C(O)N(R)_2$, $OC(O)N(R)_2$, $C(S)N(R)_2$, $(CH_2)_{0-2}N(R)C(O)R$, $(CH_2)_{0-2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R)_2$, C(O)N(OR)R, and C(=NOR)R.

In various embodiments, each $R^1$ is independently selected from the group consisting of H, halogen, —OH, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ aminoalkyl, optionally substituted $C_1$-$C_6$ haloalkoxy, and optionally substituted $C_1$-$C_6$ haloalkyl.

In various embodiments, one, and/or at least one, occurrence of $R^1$ is H. In various embodiments, one, and/or at least one, occurrence of $R^1$ is halogen (independently F, Cl, Br, or I). In various embodiments, one, and/or at least one, occurrence of $R^1$ is —OH. In various embodiments, one, and/or at least one, occurrence of $R^1$ is optionally substituted $C_1$-$C_6$ alkyl. In various embodiments, one, and/or at least one, occurrence of $R^1$ is $C_1$-$C_6$ alkyl. In various embodiments, one, and/or at least one, occurrence of $R^1$ is methyl. In various embodiments, one, and/or at least one, occurrence of $R^1$ is ethyl. In various embodiments, one, and/or at least one, occurrence of $R^1$ is n-propyl. In various embodiments, one, and/or at least one, occurrence of $R^1$ is isopropyl. In various embodiments, one, and/or at least one, occurrence of $R^1$ is n-butyl. In various embodiments, one, and/or at least one, occurrence of $R^1$ is isobutyl. In various embodiments, one, and/or at least one, occurrence of $R^1$ is sec-butyl. In various embodiments, one, and/or at least one, occurrence of $R^1$ is t-butyl. In various embodiments, one, and/or at least one, occurrence of $R^1$ is optionally substituted $C_2$-$C_6$ alkenyl. In various embodiments, one, and/or at least one, occurrence of $R^1$ is optionally substituted $C_2$-$C_6$ alkynyl. In various embodiments, one, and/or at least one, occurrence of $R^1$ is optionally substituted $C_1$-$C_6$ alkoxy. In various embodiments, one, and/or at least one, occurrence of $R^1$ is optionally substituted $C_1$-$C_6$ aminoalkyl. In various embodiments, one, and/or at least one, occurrence of $R^1$ is optionally substituted $C_1$-$C_6$ haloalkoxy. In various embodiments, one, and/or at least one, occurrence of $R^1$ is optionally substituted $C_1$-$C_6$ haloalkyl.

In various embodiments, m is 0. In various embodiments, m is 1. In various embodiments, m is 2. In various embodiments, m is 3. In various embodiments, m is 4. In various embodiments, m is 5. In various embodiments, m is 6. In various embodiments, m is 7. In various embodiments, m is 8.

In various embodiments, at each occurrence, $R^2$ and $R^3$ are independently selected from the group consisting of a bond, hydrogen, $OC(O)N(R)_2$, CN, $CF_3$, $OCF_3$, R, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, $C(O)N(R)_2$, $OC(O)N(R)_2$, $C(S)N(R)_2$, $(CH_2)_{0-2}N(R)C(O)R$, $(CH_2)_{0-2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R)_2$, C(O)N(OR)R, and C(=NOR)R.

In various embodiments, at each occurrence, $R^2$ and $R^3$ are independently selected from the group consisting of H, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ aminoalkyl, optionally substituted $C_1$-$C_6$ haloalkoxy, and optionally substituted $C_1$-$C_6$ haloalkyl.

In various embodiments, $R^2$ is H. In various embodiments, $R^2$ is optionally substituted $C_1$-$C_6$ alkyl. In various embodiments, $R^2$ is optionally substituted $C_2$-$C_6$ alkenyl. In various embodiments, $R^2$ is optionally substituted $C_2$-$C_6$ alkynyl. In various embodiments, $R^2$ is optionally substituted $C_1$-$C_6$ alkoxy. In various embodiments, $R^2$ is optionally substituted $C_1$-$C_6$ aminoalkyl. In various embodiments, $R^2$ is optionally substituted $C_1$-$C_6$ haloalkoxy. In various embodiments, $R^2$ is optionally substituted $C_1$-$C_6$ haloalkyl.

In various embodiments, $R^3$ is H. In various embodiments, $R^3$ is optionally substituted $C_1$-$C_6$ alkyl. In various embodiments, $R^3$ is optionally substituted $C_2$-$C_6$ alkenyl. In various embodiments, $R^3$ is optionally substituted $C_2$-$C_6$ alkynyl. In various embodiments, $R^3$ is optionally substituted $C_1$-$C_6$ alkoxy. In various embodiments, $R^3$ is optionally substituted $C_1$-$C_6$ aminoalkyl. In various embodiments, $R^3$ is optionally substituted $C_1$-$C_6$ haloalkoxy. In various embodiments, $R^3$ is optionally substituted $C_1$-$C_6$ haloalkyl.

In various embodiments, $R^4$ is selected from the group consisting of hydrogen, $OC(O)N(R)_2$, CN, $CF_3$, $OCF_3$, R, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, $C(O)N(R)_2$, $OC(O)N(R)_2$, $C(S)N(R)_2$, $(CH_2)_{0-2}N(R)C(O)R$, $(CH_2)_{0-2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R)_2$, C(O)N(OR)R, and C(=NOR)R.

In various embodiments, $R^4$ is selected from the group consisting of —$NH_2$, —NH($C_1$-$C_6$ alkyl), —N($C_1$-$C_6$ alkyl)($C_1$-$C_6$ alkyl), optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ aminoalkyl, optionally substituted $C_1$-$C_6$ haloalkoxy, and optionally substituted $C_1$-$C_6$ haloalkyl.

In various embodiments, $R^4$ is —$NH_2$. In various embodiments, $R^4$ is —NH($C_1$-$C_6$ alkyl). In various embodiments, $R^4$ is —N($C_1$-$C_6$ alkyl)($C_1$-$C_6$ alkyl). In various embodiments, $R^4$ is optionally substituted $C_1$-$C_6$ alkyl. In various embodiments, $R^4$ is optionally substituted $C_2$-$C_6$ alkenyl. In various embodiments, $R^4$ is optionally substituted $C_2$-$C_6$ alkynyl. In various embodiments, $R^4$ is optionally substituted $C_1$-$C_6$ alkoxy. In various embodiments, $R^4$ is $C_1$-$C_6$ alkoxy. In various embodiments, $R^4$ is methoxy. In various embodiments, $R^4$ is ethoxy. In various embodiments, $R^4$ is n-propoxy. In various embodiments, $R^4$ is isopropoxy. In various embodiments, $R^4$ is n-butoxy. In various embodiments, $R^4$ is isobutoxy. In various embodiments, $R^4$ is sec-butoxy. In various embodiments, $R^4$ is t-butoxy. In various embodiments, $R^4$ is optionally substituted methoxy. In various embodiments, $R^4$ is optionally substituted ethoxy. In various embodiments, $R^4$ is optionally substituted n-propoxy. In various embodiments, $R^4$ is optionally substituted isopropoxy. In various embodiments, $R^4$ is optionally substituted n-butoxy. In various embodiments, $R^4$ is optionally substituted isobutoxy. In various embodiments, $R^4$ is optionally substituted sec-butoxy. In various embodiments, $R^4$ is optionally substituted t-butoxy. In various embodiments, $R^4$ is optionally substituted $C_1$-$C_6$ aminoalkyl. In various embodiments, $R^4$ is optionally substituted $C_1$-$C_6$ haloalkoxy. In various embodiments, $R^4$ is optionally substituted $C_1$-$C_6$ haloalkyl.

In various embodiments, $R^2$ is absent and $R^3$ and $R^4$ combine with =C(XR')—N(R")—* to form a ring, wherein the bond marked as * is with the carbonyl group in the compound of Formula (I). In various embodiments, each occurrence of R' is independently selected from the group consisting of H, optionally substituted $C_1$-$C_6$ alkyl, optionally substituted $C_3$-$C_8$ cycloalkyl, optionally substituted aryl, optionally substituted —C(=O)-aryl, optionally substituted —C(=O)-heteroaryl, optionally substituted heteroaryl, $(CH_2)_nC(=O)R^5$, and $(CH_2CH_2O)_nC(=O)R^5$, wherein each n is independently an integer from 1 to 10. In various embodiments, each occurrence of $R^5$ is independently optionally substituted $C_3$-$C_8$ cycloalkyl, optionally substituted aryl, or optionally substituted heteroaryl. In various embodiments, X is O, S, or NR. In various embodiments, each occurrence of R" is independently selected from the group consisting of hydrogen, —NHR, —$N(R)_2$, —$NH_2$, —NH($C_1$-$C_6$ alkyl), and —N($C_1$-$C_6$ alkyl)($C_1$-$C_6$ alkyl). In various embodiments, R' is —$CH_2$—C(=O)-aryl or —$CH_2$—C(=O)-heteroaryl.

In various embodiments, X is S. In various embodiments, R' is $(CH_2)_nC(=O)R^5$. In certain embodiments, $R^5$ is phenyl. In various embodiments, n is 1. In certain embodiments, R' is

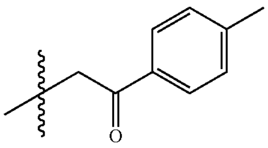

.

In various embodiments, each occurrence of R is independently hydrogen, $C_1$-$C_6$ alkyl, $C_3$-$C_8$ cycloalkyl, or phenyl. In various embodiments, two R groups bonded to a nitrogen atom or to adjacent nitrogen atoms can together with the nitrogen atom or atoms form a heterocyclyl.

In various embodiments, the compound of Formula (I) is one of the following, wherein each occurrence of $R^1$ is independently selected as described elsewhere herein:

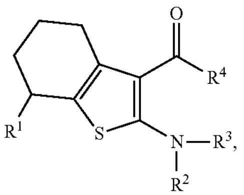
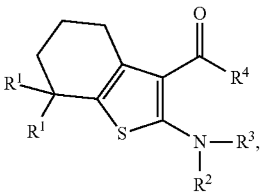
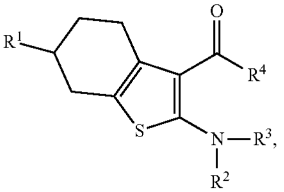
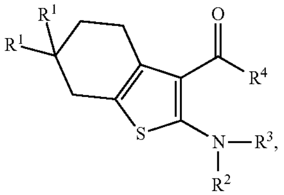
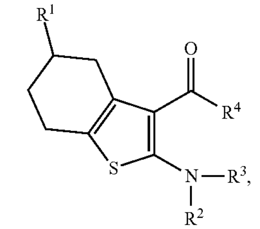
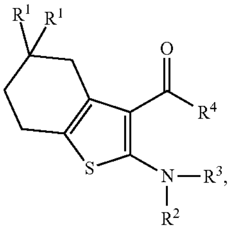
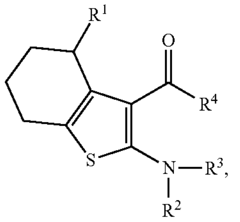
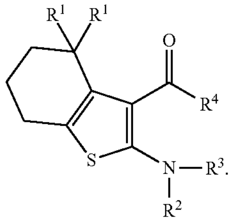

In certain embodiments, the compound of Formula (I) is selected from the group consisting of

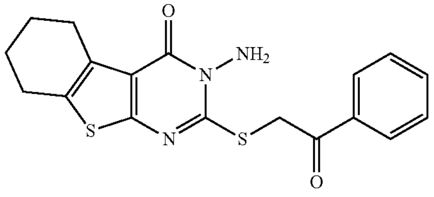 [SMILES: Nn1c(SCC(=O)c2ccccc2)nc2sc3c(c2c1=O)CCCC3]

3-amino-2-((2-oxo-2-phenylethyl)thio)-5,6,7,8-tetrahydrobenzo[4,5]thieno[2,3-d]pyrimidin-4(3H)-one,

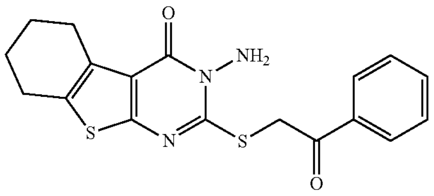 [SMILES: Nn1c(SCC(=O)c2ccccc2)nc2sc3c(c2c1=O)CCCC3]

Compound Ia, or 3-amino-5-methyl-2-((2-oxo-2-(p-tolyl)ethyl)thio)-5,6,7,8-tetrahydrobenzo[4,5]thieno[2,3-d]pyrimidin-4(3H)-one,

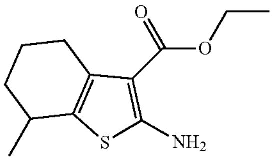 [SMILES: CCOC(=O)c1c(N)sc2c1CCCC2C]

Compound Ib, or ethyl 2-amino-7-methyl-4,5,6,7-tetrahydrobenzo[b]thiophene-3-carboxylate,

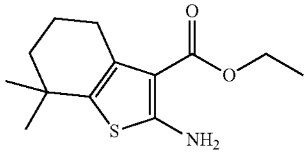 [SMILES: CCOC(=O)c1c(N)sc2c1CCCC2(C)C]

ethyl 2-amino-7,7-dimethyl-4,5,6,7-tetrahydrobenzo[b]thiophene-3-carboxylate,

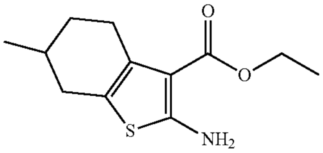 [SMILES: CCOC(=O)c1c(N)sc2c1CCC(C)C2]

ethyl 2-amino-6-methyl-4,5,6,7-tetrahydrobenzo[b]thiophene-3-carboxylate,

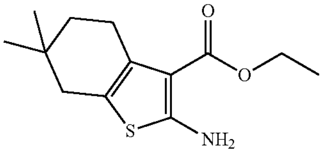 [SMILES: CCOC(=O)c1c(N)sc2c1CCC(C)(C)C2]

ethyl 2-amino-6,6-dimethyl-4,5,6,7-tetrahydrobenzo[b]thiophene-3-carboxylate,

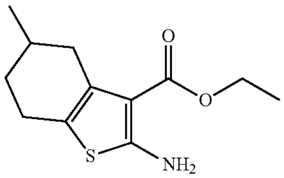

ethyl 2-amino-5-methyl-4,5,6,7-tetrahydrobenzo[b]thiophene-3-carboxylate,

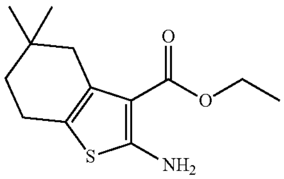 [SMILES: CCOC(=O)c1c(N)sc2c1CC(C)(C)CC2]

ethyl 2-amino-5,5-dimethyl-4,5,6,7-tetrahydrobenzo[b]thiophene-3-carboxylate,

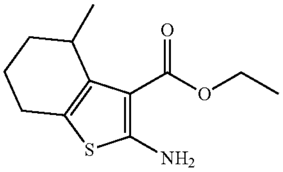 [SMILES: CCOC(=O)c1c(N)sc2c1C(C)CCC2]

ethyl 2-amino-4-methyl-4,5,6,7-tetrahydrobenzo[b]thiophene-3-carboxylate,

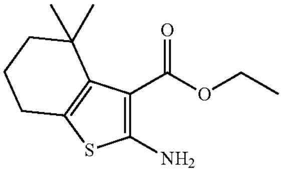 [SMILES: CCOC(=O)c1c(N)sc2c1C(C)(C)CCC2]

ethyl 2-amino-4,4-dimethyl-4,5,6,7-tetrahydrobenzo[b]thiophene-3-carboxylate, and

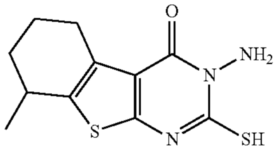 [SMILES: CC1CCCc2c1sc1nc(S)n(N)c(=O)c21]

Compound Ic, or 3-amino-2-mercapto-8-methyl-5,6,7,8-tetrahydrobenzo[4,5]thieno[2,3-d]pyrimidin-4(3H)-one.

In various embodiments, the invention provides one of the following compounds of Formula (I-A), or a salt, solvate, stereoisomer, geometric isomer, and/or tautomer thereof:

Formula (A-1)

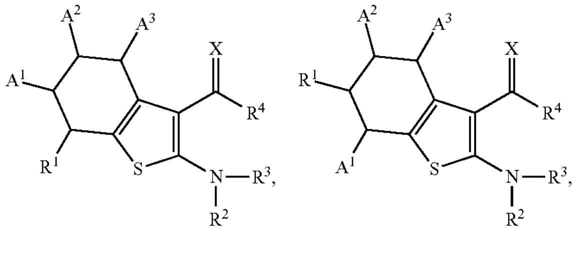

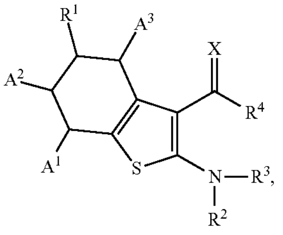

or

-continued

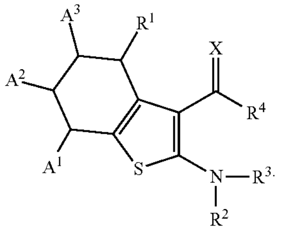

In any compound of Formula (A-1), $R^1$, $A^1$, $A^2$, and $A^3$ represents one or two independent substitutions, and $A^1$, $A^2$, and $A^3$ are each independently defined as $R^1$ herein, and X is selected from O, S, or NR. In certain embodiments, X is S. In various embodiments, $A^1$, $A^2$, and $A^3$ are all ($H_2$) so that the cyclohexyl ring in the compound is unsubstituted at positions $A^1$, $A^2$, and $A^3$.

In various embodiments, the compound is a compound of Formula (II), or a salt, solvate, stereoisomer, geometric isomer, and/or tautomer thereof:

(II)

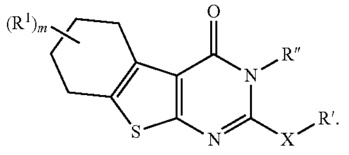

In various embodiments, the compound is one of the following compounds or a salt, solvate, stereoisomer, geometric isomer, and/or tautomer thereof:

(B-1)

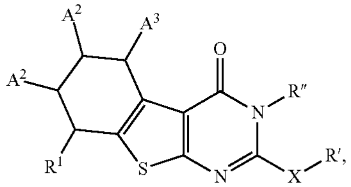

(B-2)

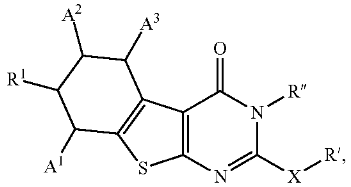

(B-3)

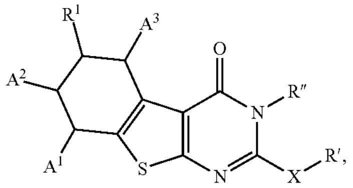

or

-continued (B-4)

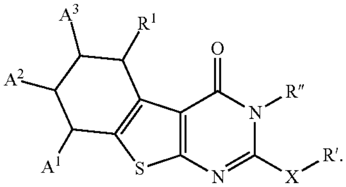

The Glucagon-like peptide 1 receptor (GLP-1R) belongs to the family of G-protein-coupled receptors (GPCRs). In certain embodiments, the compound of Formula (I) is a Glucagon-like peptide 1 receptor (GLP-1R) agonist. In certain embodiment, the compound is a positive allosteric modulator (PAM) of GLP-1R. In certain embodiments, the compound selectively enhances GLP-1R activity. In certain embodiments, the compound has no significant effect on the activity of other G-protein-coupled receptors (GPCRs).

Targeting the allosteric sites on GLP-1R represents a promising strategy for the development of small molecule drugs that can offer several potential benefits and help overcome problems associated with GLP-1 peptide drugs. However, due to the lack of 3D structure information for GLP-1R until very recently, past small molecule drug discovery efforts were often initiated by high-throughput screening. In past, it was attempted to take the rational design approach by first constructing a 3D model of the TM domain of GLP-1R in its active conformation, then performing in silico structure-based screening. Through in vitro experiments, one compound M-4 was shown to function as a potential ago-PAM.

Figure 7:
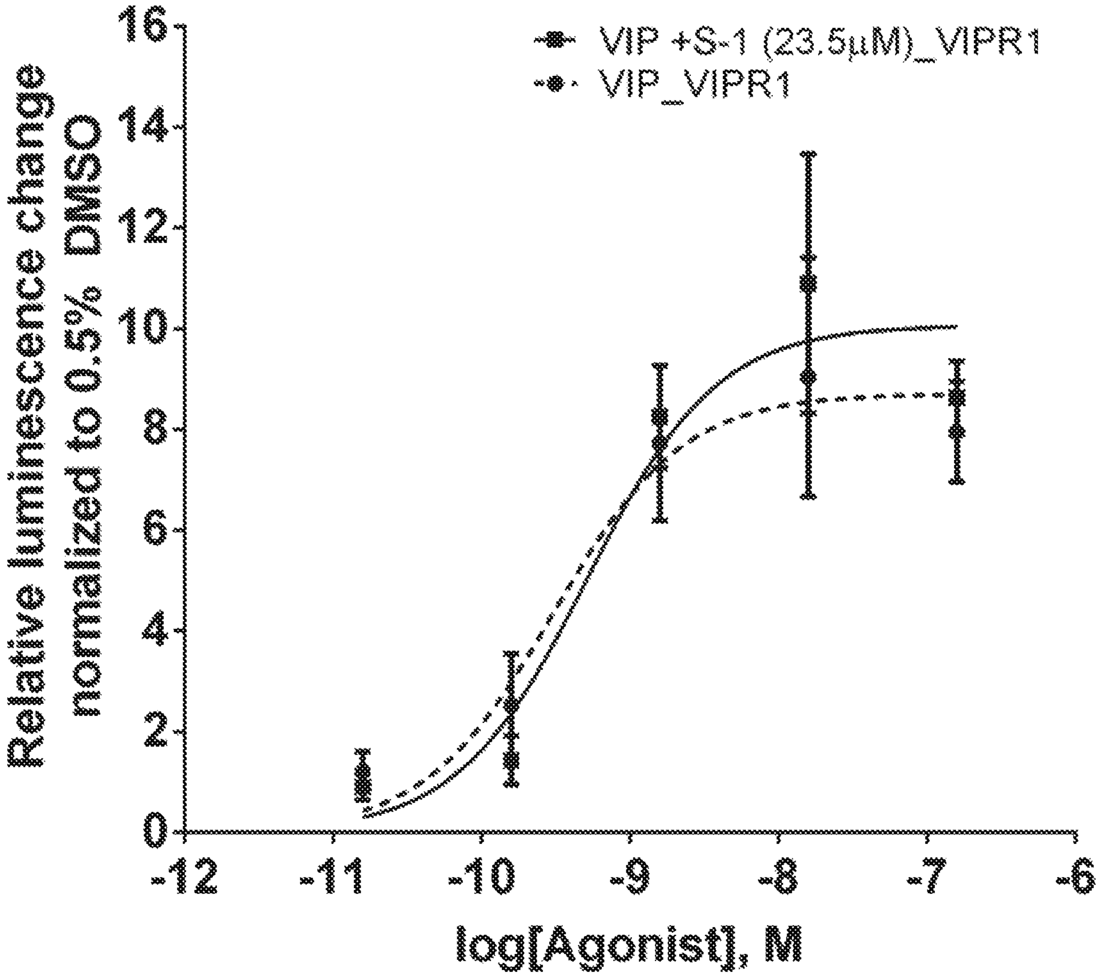
FIG. 7 is a graph showing potential non-specific activity of Compound Ib on VIPR1. VIPR1 activation were assessed as luminescence normalized to protein concentration and plotted as luminescence fold change with respect to vehicle control (0.5% DMSO). Data are average of three independent experiments with at least three technical replicates for each conditions and error bars for each concentration were plotted as SEM (n=3). Statistical analysis was done using 2-way ANOVA. The comparison was done between the corresponding data points on the two-dose response curve generated due to the effect of GLP-1 alone and in combination with Compound Ib.

In the current work, the structure-based molecule design was carried out using the cryo-EM structure of the GLP-1R in its active state and identified one compound (Ia) as an ago-PAM of GLP-1R. Upon confirming the binding site of Ia through site-specific mutagenesis studies (FIG. 5A-5C), structure-based lead optimization were performed, followed by medicinal synthesis. The combined approach has led to the discovery of two novel PAMs (Ib and Ic). All three compounds (Ia, Ib and Ic) are structurally and chemically different from those reported in the literature. Further, they all have small molecular weight (<400 for Ia, 239 for Ib and 267 for Ic) with Ib and Ic being the smallest known PAMs of GLP-1R. When applied in combination with GLP-1 to the HEK293 cells overexpressing VIPR1, Ib did not induce non-specific activity on this receptor (FIG. 7). Given its small molecular weight, low x Log P value, demonstrated specificity towards GLP-1R, and excellent capability in stimulating insulin secretion (FIG. 8), compound Ib emerges as an excellent lead compound.

The discovery of small molecule PAMs of GLP-1R using the rational structure-based approach as demonstrated here further validates the feasibility of this approach in the small molecule drug discovery of other members of the pharmaceutical important Class B family of GPCRs. All of the endogenous ligands for the Class B GPCRs are moderately long peptide hormones which bind to their receptors in a similar manner as GLP-1. The nature of these binding sites makes it challenging for designing small molecule binding to these sites. With existence of the allosteric sites being confirmed for more and more Class B GPCRs, targeting these allosteric sites using structure-based drug design techniques represents a new venue for the development of small molecule drugs agonists targeting these Class B GPCRs through allosteric regulations.

In another aspect, the invention provides a composition comprising at least one pharmaceutically acceptable carrier and the compound of the invention, or a salt, solvate, stereoisomer, geometric isomer, and/or tautomer thereof.

In certain embodiment, the composition of the invention is formulated for administration by a route selected from the group consisting of oral, parenteral, transdermal, transmucosal, intravesical, intrapulmonary, intraduodenal, intragastrical, intrathecal, subcutaneous, intramuscular, intradermal, intra-arterial, intravenous, intrabronchial, inhalation, and topical.

In certain embodiments, the composition further comprising at least one additional agent useful for treating, ameliorating, or preventing diabetes and/or insulin resistance in a subject.

In certain embodiments, the at least one additional agent is selected from the group consisting of α-glucosidase inhibitor, lipase inhibitor, sulfonyl urea, meglitinide, biguanide, thiazolidinedione, pramlintide, incretin mimetic, DPP-IV inhibitor, and SGLT2 inhibitor.

The compounds of the invention can possess one or more stereocenters, and each stereocenter can exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention may exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal. In certain embodiments, protective groups are removed by acid, base, reducing conditions (such as, for example, hydrogenolysis), and/or oxidative conditions.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react. Typically blocking/protecting groups may be selected from:

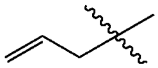
allyl

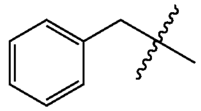
Bn

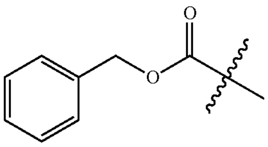
Cbz

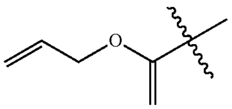
alloc

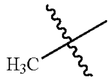
Me

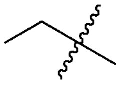
Et

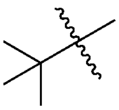
t-butyl

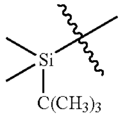
TBDMS

-continued

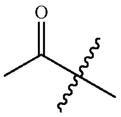
acetyl

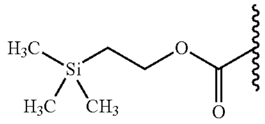
Teoc

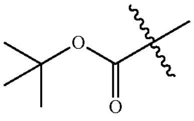
Boc

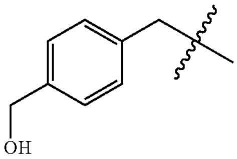
PMB

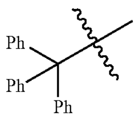
trityl

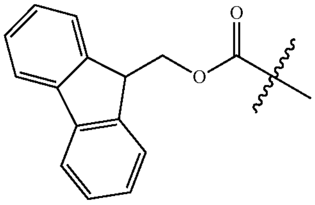
Fmoc .

Other protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

Methods

The invention includes a method of treating, ameliorating, or preventing insulin resistance in a subject in need thereof by administering to the subject a therapeutically effective amount of the compound of the invention. The invention further includes a method of treating, ameliorating, or preventing diabetes in a subject in need thereof by administering to the subject a therapeutically effective amount of the compound of the invention. In certain embodiments, the diabetes is type II diabetes. In certain embodiment, the compound is administered as a therapeutic composition. The compound and the compositions are as described elsewhere herein.

In other embodiments, the method further comprises administering to the subject an additional therapeutic agent that treats, ameliorates, or prevents insulin resistance and/or diabetes. In certain embodiment, the additional therapeutic agent is as described elsewhere herein.

In certain embodiments, administering the compound of the invention to the subject allows for administering a lower dose of the additional therapeutic agent compared to the dose of the additional therapeutic agent alone that is required to achieve similar results in treating, ameliorating, or preventing insulin resistance and/or diabetes. For example, in other embodiments, the compound of the invention enhances the activity of the additional therapeutic compound, thereby allowing for a lower dose of the additional therapeutic compound to provide the same effect.

In certain embodiments, the compound of the invention and the additional therapeutic agent are co-administered to the subject. In other embodiments, the compound of the invention and the additional therapeutic agent are coformulated and co-administered to the subject.

In certain embodiments, the subject is a mammal. In other embodiments, the mammal is a human.

Combination Therapies

The compounds useful within the methods of the invention can be used in combination with one or more additional agents useful for treating or preventing diabetes and/or insulin resistance. These additional agents can comprise compounds that are commercially available or synthetically accessible to those skilled in the art. These additional agents are known to treat, prevent, or reduce the symptoms of diabetes and/or insulin resistance.

Non-limiting examples of anti-diabetic medications contemplated within the invention include:

α-glucosidase inhibitors: inhibit upper GI enzymes (α-glucosidases) responsible for digesting carbohydrates, slowing absorption of glucose; also cause slower rise in postprandial blood glucose concentrations. Non-limiting examples: acarbose (Precose, Glucobay); miglitol (Glyset); voglibose (Vogseal, Volix, Basen);

lipase inhibitors: inhibit pancreatic and gastric lipases, blocking fat absorption. Non-limiting examples: orlistat (Xenical, Alli);

sulfonyl ureas: act as insulin secretagogues, triggering insulin release by interacting with the ATP-dependent potassium channel of the pancreatic β-cells. The net result is that more insulin is released at all blood glucose concentrations. They are the most commonly used drugs for treatment of patients with type 2 diabetes, but, since they trigger release of insulin itself, the combination of insulin & sulfonyl ureas is not common. Non-limiting examples: $1^{st}$ generation of sulfonyl ureas-acetohexamide, chlorpropamide (Diabinese), tolbutamide (Orinase), tolazamide; $2^{nd}$ generation of sulfonyl ureas-gliclazide (Diamicron R, Diamicron MR), glyburide or glibenclamide (Diabeta, Micronase, Glynase), glipizide (Glucotrol, Glucotrol XL), glimepiride (Amaryl), gliquidone (Glurenorm);

meglitinides: short-acting glucose-lowering drugs, acting by regulating ATP-dependent potassium channels in pancreatic B-cells like sulfonyl ureas; structurally different from sulfonylureas and act via different receptors as well. Non-limiting examples: mitiglinide (Glufast); nateglinide (Starlix); repaglinide (Prandix);

biguanides: reduce glucose release from the liver and increase glucose uptake by skeletal muscle. Metformin is the preferred initial treatment of type 2 diabetes, with good glycemic efficacy, absence of weight gain and hypoglycemia, general tolerability and low cost. The combination of metformin & insulin is generally associated with lower weight gain than insulin by itself or the combination of insulin & sulfonylureas. The triple combination of a sulfonyl urea, metformin and insulin glargine has been shown to have fewer adverse effects, fewer lipid profile problems and lower cost than the triple combination of a sulfonyl urea, metformin and rosiglitazone. Non-limiting examples: metformin (Glucophage); phenformin (DBI); buformin (Glybigid, Glybigidum);

thiazolidinediones: increase insulin sensitivity by acting on adipose, muscle and liver tissue to increase glucose utilization and decrease glucose production. The mechanism of action is not fully understood, but they seem to bind and activate one or more peroxisome proliferator-activated receptors (PPARs), regulating gene expression. Non-limiting examples: rosiglitazone (Avandia); pioglitazone (Actos); troglitazone (Rezulin); tesaglitazar (Pargluva);

pramlintide (Symlin): also known as islet amyloid polypeptide, is a synthetic analog of human amylin that slows gastric emptying and suppresses glucagon, reducing postprandial rises in blood glucose levels; approved by the FDA to lower blood sugar in type 1 diabetes patients;

incretin mimetics: these insulin secretagogues act as glucagon-like peptide-1 (GLP-1) membrane-receptor agonists. They act in a glucose-dependent manner, stimulating insulin secretion only when blood glucose levels are higher than normal. They also promote β-cell regeneration in animal models. Incretin mimetics decrease gastric motility and cause nausea. Non-limiting examples: exenatide, exedin-4 or AC2993 (Byetta); liraglutide, NN2211, or NNC 90-1170; it consists of a lipid conjugate of GLP-1, with high protein binding and a half-life of ~10 h in man;

DPP-IV inhibitors: affect glucose regulation, inhibiting degradation of GLP-1. They generally cause fewer problems with hypoglycemia or weight gain as compared to standard treatments. Non-limiting examples: sitagliptin (Januvia); sitagliptin & 36826614.3-32-metformin (Janumet); vildagliptin (Galvus); vildagliptin & metformin (Eucreas);

SGLT2 inhibitors: they supress SGLT2 protein, causing excess glucose to be excreted from the body rather than reabsorbed. Non-limiting examples: dapaglifozin.

A synergistic effect can be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations can be administered to the subject either prior to or after the onset of insulin resistance and/or diabetes. Further, several divided dosages, as well as staggered dosages can be administered daily or sequentially, or the dose can be continuously infused, or can be a bolus injection. Further, the dosages of the therapeutic formulations can be proportionally increased or decreased as indicated by the exigencies of the therapeutic or prophylactic situation.

Administration of the compositions of the present invention to a patient, preferably a mammal, more preferably a human, can be carried out using known procedures, at dosages and for periods of time effective to treat, ameliorate, or prevent insulin resistance and/or diabetes. An effective amount of the therapeutic compound necessary to achieve a therapeutic effect may vary according to factors such as the state of the disease or disorder in the patient; the age, sex, and weight of the patient; and the ability of the therapeutic compound to treat, ameliorate, or prevent insulin resistance and/or diabetes. Dosage regimens can be adjusted to provide the optimum therapeutic response. For example, several divided doses can be administered daily or the dose can be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention can be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of heart failure in a patient.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier can be a solvent or dispersion medium containing, for example, water, ethanol, polyol (for example, glycerol, propylene glycol, and liquid polyethylene glycol, and the like), suitable mixtures thereof, and vegetable oils.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration can be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 350 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of insulin resistance and/or diabetes.

Formulations can be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention can be formulated for administration by any suitable route, such as for oral or parenteral, for example, transdermal, transmucosal (e.g., sublingual, lingual, (trans) buccal, (trans) urethral, vaginal (e.g., trans- and perivaginally), (intra) nasal and (trans) rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use can be prepared according to any method known in the art and such compositions may contain one or more agents selected from the group consisting of inert, non-toxic pharmaceutically excipients that are suitable for the manufacture of tablets.

Such excipients include, for example an inert diluent such as lactose; granulating and disintegrating agents such as cornstarch; binding agents such as starch; and lubricating agents such as magnesium stearate. The tablets can be uncoated or they can be coated by known techniques for elegance or to delay the release of the active ingredients. Formulations for oral use may also be presented as hard gelatin capsules wherein the active ingredient is mixed with an inert diluent.

Parenteral Administration

For parenteral administration, the compounds of the invention can be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents can be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. patents application Ser. Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention can be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time can be as long as a month or more and should be a release which is longer that the same amount of agent administered in bolus form.

For sustained release, the compounds can be formulated with a suitable polymer or hydrophobic material which provides sustained release properties to the compounds. As such, the compounds for use the method of the invention can be administered in the form of microparticles, for example, by injection or in the form of wafers or discs by implantation.

In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of heart failure in the patient being treated. The skilled artisan is able to determine appropriate dosages depending on these and other factors.

A suitable dose of a compound of the present invention can be in the range of from about 0.01 mg to about 5,000 mg per day, such as from about 0.1 mg to about 1,000 mg, for example, from about 1 mg to about 500 mg, such as about 5 mg to about 250 mg per day. The dose can be administered in a single dosage or in multiple dosages, for example from 1 to 4 or more times per day. When multiple dosages are used, the amount of each dosage can be the same or different. For example, a dose of 1 mg per day can be administered as two 0.5 mg doses, with about a 12-hour interval between doses.

It is understood that the amount of compound dosed per day can be administered, in non-limiting examples, every day, every other day, every 2 days, every 3 days, every 4 days, or every 5 days. For example, with every other day administration, a 5 mg per day dose can be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the invention can be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

The disclosures of each and every patent, patent application, and publication cited herein are hereby incorporated herein by reference in their entirety. While this invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Materials

The approach presented here includes several steps: (i) In silico structure-based ligand screening and molecular design; (ii) Chemical synthesis of the designed compounds; and (iii) Experimental validation of the PAM effects of small molecule compounds.

In Silico Structure-Based Approach

Structure-Based Screening

The cryo-EM structure of rabbit GLP-1R in its active conformation (PDB ID: 5VAI), which has 94% sequence identity with human GLP-1R, was imported in MOE (Molecular Computing Group Inc. version 2018.01), and all hetero atoms, water molecules, Gs protein and the N-terminal domain of the receptor were deleted. Energy minimization was subsequently carried out on the remaining structure using the default settings in MOE. The potential allosteric sites in the 7TM of the GLP-1R was predicted using the SiteFinder module with the default setting in MOE. All the predicted binding sites were manually inspected and the one different from the orthosteric site and with the largest binding volume except for the orthosteric site was chosen as the potential allosteric site in the screening practices below.

For in silico screening, the same cryo-EM structure of rabbit GLP-1R (PDB ID: 5VAI) was imported in the Schrodinger Suite (version 2017). The receptor was cropped to retain only its 7TM and was prepared using in Protein Preparation Wizard with default settings. The protein grid was prepared using the Receptor Grid Generation Panel with the default settings and the rotation of hydroxyl group was not allowed. The grid center was kept at (124.2, 132.0, 122.0) with the dimensions of inner grid box as 10 Å×10 Å×10 Å and of outer grid box as 30 Å×30 Å×30 Å. The prepared GLP-1R grid was then used for ligand docking. The same library of 5,689 drug-like molecules identified in the previous work that have similar ligand properties with the 23 active compounds of GLP-1R were prepared using LigPrep module. The prepared ligands were then docked to the receptor grid using Glide SP mode with default settings. Sixteen different compounds with the highest docking scores were re-docked to the same receptor grid using Glide XP mode and then Induced Fit mode. Top-ranked molecules with the smallest molecular weight and the small log P value was chosen for in vitro test.

Structure-Based Molecular Design

The lead compound identified through in silico screening and experimentally confirmed by in vitro test was further optimized in the Schrodinger Suite (version 2017). First, the R-groups were generated using Interactive Enumeration Module in the Schrodinger Suite. Next, the chemical structure of the lead compound was used as the scaffold and its H-atoms were replaced by the various R-groups one at a time or in combination. The newly generated compounds were then docked to the same site using Glide Induced Fit mode as described previously. Top-ranked compounds with small molecular weight were chosen for consideration of synthesis.

Medicinal Synthesis of Newly Designed Compounds

Chemicals were purchased from Oakwood Products Inc. (West Columbia, SC), Sigma Aldrich (St. Louis, MO), TCI America (Portland, OR), and Alfa Aesar (Ward Hill, MA). All chemicals were used as purchased. None of the active compounds (Ia, Ib and Ic) were identified as PAIN compounds and all three show a purity≥95%.

Ethyl 2-amino-7-methyl-4,5,6,7-tetrahydrobenzo[b]thiophene-3-carboxylate, Ib. 3.2 g sulfur, 11 mL cyanoacetic ethyl ester, and 10 mL of 4-methylcyclohexanone was added at room temperature (25° C.) to a round bottom flask containing 20 mL of ethanol. The reaction mixture was stirred for 10 minutes, then 8 mL of diethylamine was added dropwise. The reaction was stirred at room temperature for 12 hours, then vacuum filtered and rinsed with water: ethanol (1:1) three times. The filtrate was a light yellow solid (60% yield). 1H NMR (400 MHz, $d_6$-DMSO): 7.2 (1H, $NH_2$, s), 4.15 (2H, —$OCH_2CH_3$, m), 2.8 (1H, dd), 2.45 (2H, m), 2.1 (1H, m), 1.7 (2H, m), 1.3 (1H, m), 1.24 (3H, —$OCH_2CH_3$, t), 0.99 (3H, —$CH_3$, d).

Ethyl 7-methyl-2-(((methylthio)carbonothioyl) amino)-4,5,6,7-tetrahydrobenzo[b]thiophene-3-carboxylate To a vigorously stirred solution of ethyl 2-amino-7-methyl-4,5,6,7-tetrahydrobenzo[b]thiophene-3-carboxylate (4.5 g, 0.02 mol) in dimethyl sulfoxide (10 mL) at room temperature, carbon disulfide (1.98 g, 0.026 mol) and aqueous sodium hydroxide (1.2 mL, 20 mol solution) were added simultaneously over 30 min. Then the mixture was allowed to stir for 30 min more. Dimethyl sulfate (2.5 g, 0.02 mol) was added dropwise to the reaction mixture with stirring at 5-10° C., it was further stirred for 2 h and then poured into ice water; the solid obtained was filtered, dried, and recrystallized from ethanol. The filtrate was a light yellow solid (75% yield). $^1$H NMR (400 MHz, $CDCl_3$): 13.0 (1H, NH, s), 4.4 (2H, —$OCH_2CH_3$, m), 3.0 (1H, dd), 2.8 (3H, S—$CH_3$, S), 2.7-1.8 (6H, m), 1.4 (3H, —$OCH_2CH_3$, t), 1.1 (3H, —$CH_3$, d).

3-amino-2-mercapto-8-methyl-5,6,7,8-tetrahydrobenzo[4,5]thieno[2,3-d]pyrimidin-4(3H)-one, Ic A solution of ethyl 7-methyl-2-(((methylthio)carbonothioyl)amino)-4,5,6,7-tetrahydrobenzo[b]thiophene-3-carboxylate-(3.15 g, 0.01 mol) in ethanol 30 mL was treated with hydrazine hydrate (4.3 g, 0.01 mol, 99%) and refluxed on a water bath until the methylmercaptan evolution ceased (8 h). After cooling, the solid obtained was filtered, dried, and washed with ethanol. The filtrate was used without further purification (70% yield). IR: 3280, 3230 (NH2), 2650 (SH), 1645 $cm^{-1}$ (C═O). $^1$H NMR (400 MHz, $CDCl_3$): 6.2 (1H, $NH_2$, s), 3.2 (1H, dd), 3.0 (1H, dd), 2.8-1.8 (6H, m), 1.9 (3H, m), 1.1 (3H, —$CH_3$, d).

4-(2-((3-amino-8-methyl-4-oxo-3,4,5,6,7,8-hexahydrobenzo[4,5]thieno[2,3-d]pyrimidin-2-yl)thio)acetyl) benzonitrile 2 mmol (0.5 g) of 3-amino-2-mercapto-8-methyl-5,6,7,8-tetrahydrobenzo[4,5]thieno[2,3-d]pyrimidin-4(3H)-one, 4-(2-bromoacetyl)benzonitrile (2 mmol), and 2.5 mmol sodium acetate was refluxed in 10 mL of methanol for 8 hours. The reaction mixture was allowed to cool, vacuum filtered, and washed with ethanol. The filtrate was obtained as a white solid. (70% yield). $^1$H NMR (400 MHz, do-DMSO): 8.2 (2H, H—Ar, d), 8.1 (2H, H—Ar, d), 5.8 (2H, $NH_2$, s), 4.6 (1H, s), 3.05 (1H, dd), 2.65 (2H, m), 2.4 (3H, $CH_3$—Ar, s), 1.8 (2H, m), 1.4 (1H, m), 1.0 (3H, —$CH_3$, d).

In Vitro Testing of Potential GLP-1R PAMs by CRE Luciferase Reporter Assay

Materials

HEK293 cell stably expressing CRE/CREB luciferase reporter gene (BPS Bioscience #60515), RPMI medium (Corning #10-040), Krebs Ringer Bicarbonate buffer (Amsbio #KRB-1000), L-Glutamine (Gibco #25030-081), HEPES (Gibco #15630-080), Sodium Pyruvate (Gibco #11360-070), β-mercaptoethanol (MP #806444), D-Glucose (#G-7528), Fetal Bovine Serum (Fisher #03600511), penicillin/streptomycin (Corning #30-002-C1), Hygromycin B (Alfa Aesar #J60681), Lipofectamine 2000 (Invitrogen #11668027), VIPR peptide agonist (Sigma #V3628), VIPR peptide antagonist (Sigma #SCP0260), GLP-1R peptide agonist (Sigma #9416), 6 well cell culture plates (Ultra Cruz #sc-204443), 96 well cell culture plates (Sigma #CLS9102), Luciferase cell culture lysis reagent (Promega #E1531), Luciferase assay reagent (Promega #E1501), and Ultra-Sensitive Rat Insulin Kit (Crystal Chem #90060) were purchased from vendors. VIPR1 receptor plasmid (#51865) was purchased from Addgene, Flag-tagged Human GLP-1R and Flag-tagged pCMV-N-Flag negative control vector were purchased from vendors (Sino Biological Inc. #HG13944-NF and #CV061) and INS-1832/13 cells were provided by Dr. Xianxin Hua at Perelman School of Medicine, Pfu DNA polymerase kit (Thermofisher #EP0501) and primers (University of Pennsylvania) were purchased from vendors, plasmid of mutant human GLP-1R S352A and V332W was kindly provided by iHuman Institute, Shanghai Tech University.

Transfection and Cell Culture

HEK293 cells stably expressing CRE/CREB Reporter (luciferase) were cultured in RPMI medium supplemented with 8% (v/v) fetal bovine serum, 2% (v/v) penicillin/streptomycin, and 100 μg/ml of Hygromycin B. Cells were maintained in an incubator at 37° C. with 5% $CO_2$. Cells were seeded into 6-well cell culture plates one day before transfection. After overnight incubation, one well of cell was transiently transfected with 3.4 μg of human GLP-1R or empty vector, respectively, using lipofectamine 2000. After 4 hours of transfection, transfection medium was replaced by RPMI medium supplemented with 5% (v/v) fetal bovine serum and 2% (v/v) penicillin/streptomycin. After 24 hours of incubation, cells were trypsinized and seeded into 96 well cell culture plates (5.5× $10^4$ cells per well) and maintained at 37° C. in 5% $CO_2$ incubator for 24 hours. The cells were starved using RPMI with 0.5% sera. After 24 hours of starvation, the transfected cells were treated with compounds as indicated.

Luciferase Assay

Compounds dissolved in 100% DMSO were diluted to indicated concentration in RPMI 1640 (0.5% DMSO included for all cell culture). After 4 hours of treatment, cells were harvested by cold luciferase cell culture lysis buffer and kept on shaker for 10 min at 4° C. Luciferase activity was measured using luciferin substrate and luminescence was read by Wallac 1420 multiplate reader. Luciferase activity of HEK293 reporting cells cultured using 0.5% DMSO and full RPMI medium was used as a vehicle control. Protein concentration of each well was determined by Bradford assay.

Non-Specific Effect of GLP-1R PAM on Vasoactive Intestinal Polypeptide Receptor 1 (VIPR1)

HEK293 cells stably expressing CRE/CREB Reporter (luciferase) were cultured in RPMI 1640 supplemented with 8% (v/v) fetal bovine serum, 2% (v/v) penicillin/streptomycin, and 100 μg/ml of Hygromycin B. Cells were maintained at 37° C. with 5% $CO_2$. Cells were seeded into 6-well cell culture plates one day before transfection. After overnight incubation, cells were transiently transfected with 3.4 μg of VIPR1, using Lipofectamine 2000. After 4 hours of transfection, medium was replaced by RPMI supplemented with 5% (v/v) fetal bovine serum. After 24 hours of incubation, cells were trypsinized and seeded into 96 well cell culture plates (5.5×$10^4$ cells per well) and maintained at 37° C. in 5% $CO_2$ for 24 hours. After 24 hours of incubation, the cells were starved with RPMI with 0.5% sera. After 24 hours of starvation, the transfected cells were treated with compounds as indicated.

Site Specific Mutagenesis of Human GLP-1R

Based on the docking pose of the lead compound, the desired mutation of N406 to A was introduced into N-Flag tag-labeled human GLP-1R using site directed mutagenesis by traditional PCR method using forward primer (SEQ ID NO:1; 5'-TTATACTGCTTTGTCgccAATGAGGTCCAGCTG-3') and reverse primer (SEQ ID NO:2; 5'-CAGCTGGACCTCATTggcGACAAAGCAGTATAA-3'). The PCR product was then treated with Dpn1 enzyme. The introduction of desired mutation in human GLP-1R plasmid was confirmed by DNA sequencing. The mutants S352A and V332W were kindly provided by Shanghai Tech University. These constructs were used to express mutant GLP-1R in HEK293-CREB luciferase cells.

Glucose Stimulated Insulin Production in INS-1 832/13 Cells

INS-1 832/13 cells were cultured in RPMI 1640 supplemented with 2 mM L-glutamine, 1 mM sodium pyruvate, 10% FBS, 10 mM HEPES, 100 units/ml penicillin, 100 μg/ml streptomycin, and 50 μM β-mercaptoethanol. Cells were maintained in an incubator at 37° C. with 5% $CO_2$. To determine the effect of GLP-1R agonist Ia and PAM Ib on insulin production, INS-1 cells were seeded onto 24 well plates. After 48 hours of incubation, cells were washed twice with 200 μl of Krebs-Ringer Bicarbonate (KRB) buffer and starved for 2 hours in fresh KRB supplemented with 0.1% serum. After 2 hours of starvation, the buffer was replaced with 200 μl of KRB containing 0.1% serum, 16.7 mM glucose and 9.7 μM of Ia/11.75 μM of Ib, or 181 nM of GLP-1 with 0.125% DMSO or 0.125% DMSO alone (vehicle control) and incubated at 37° C. with 5% $CO_2$. After 20 minutes, the supernatant was collected, centrifuged at 1000 rpm for 5 min at 4° C., and aliquoted and stored at −20° C. These samples were used to determine insulin concentration using insulin detection kit ELISA following the manual.

Data Analysis:

The concentration-dependent dose response curve was generated using Graph Pad Prism 6.0 for Mac (GraphPad Software Inc., San Diego, CA). The curves were fitted based on sigmoidal dose response with the bottom parameter being kept 0. The $EC_{50}$ value was calculated from Prism. The statistical difference between different groups was analyzed by 2-way ANOVA module in Prism.

Figure 1A:
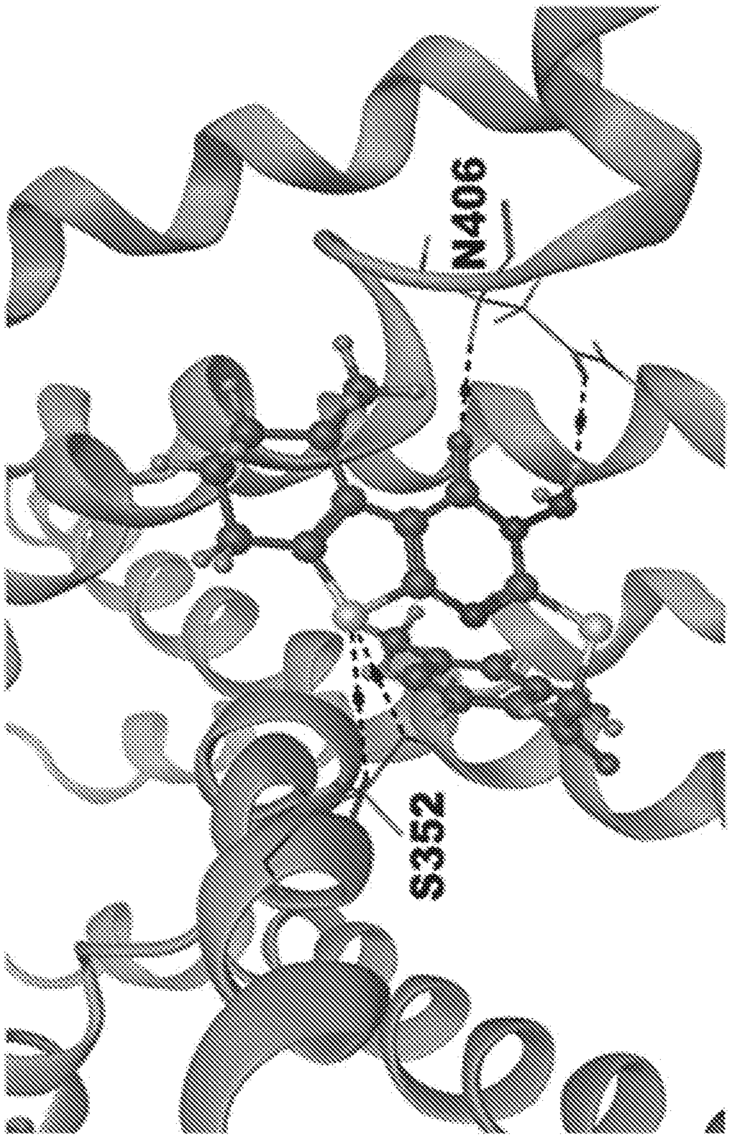
Figure 2:
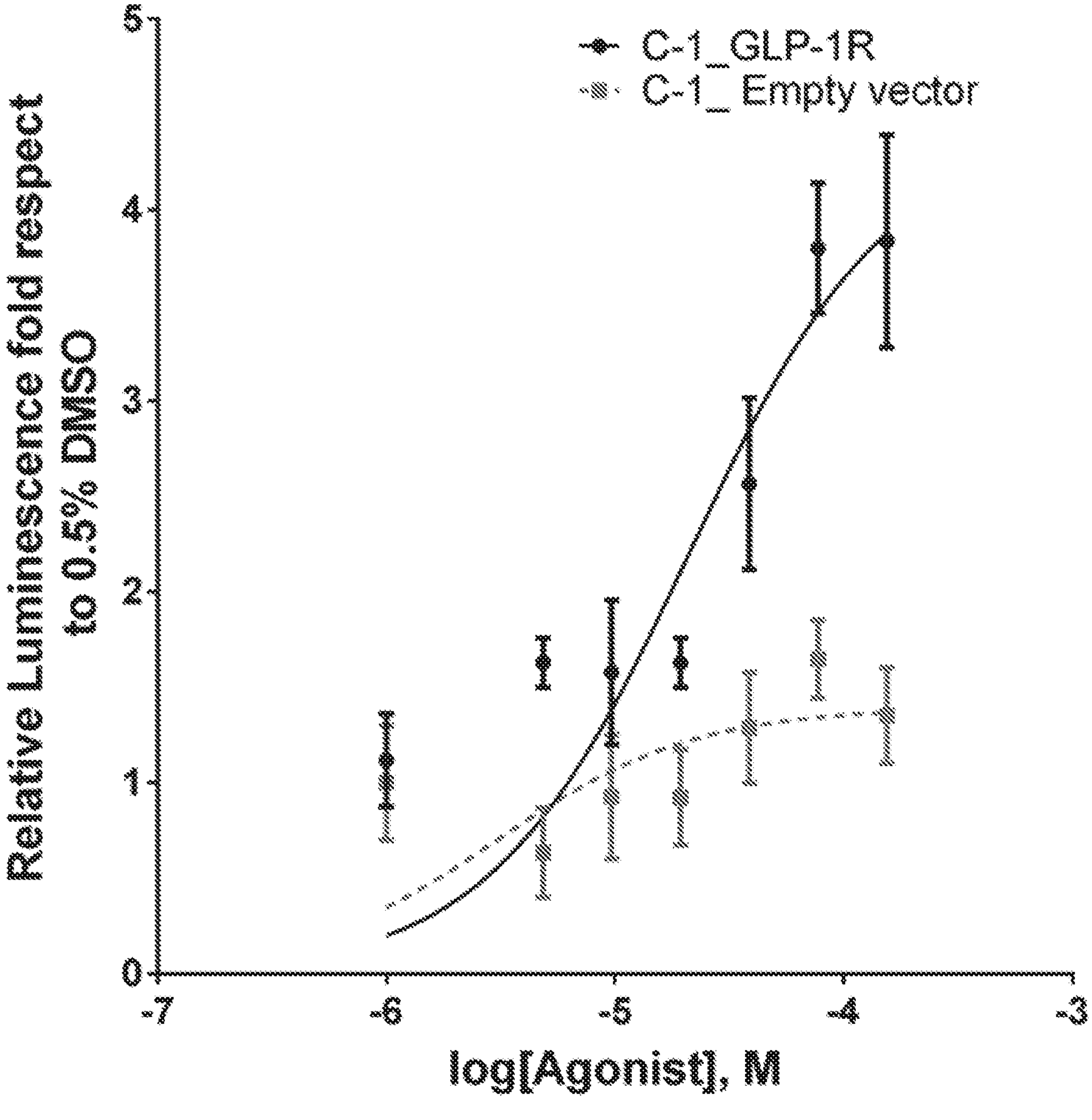
FIG. 2 is a graph showing in vitro agonistic activity of Compound Ia in HEK293 cells co-expressing human GLP-1R and a 3xcAMP response element-luciferase reporter. Dose-response curves of Compound Ia (C-1) in the presence and absence of human GLP-1R, respectively ($EC_{50}$=21 μM). HEK293-CREB luciferase cell line transiently expressing human GLP-1R or empty vector was treated with different concentrations of Compound Ia. GLP-1R activation was measured as the amount of luminescence produced, which was normalized by respective protein concentrations. The background effect of Compound Ia was measured as the amount of luminescence produced in HEK293 cells expressing empty vector, which was normalized by protein concentration. In all experiments, normalized luminescence was plotted with respect to vehicle control (0.5% DMSO). The dose response curves were generated using sigmoidal dose response parameter from GraphPad Prism 6.0. Data are average of three independent experiments with at least three technical replicates for each treatment conditions and error bars for each concentration were plotted as SEM (n=3).
Figure 3:
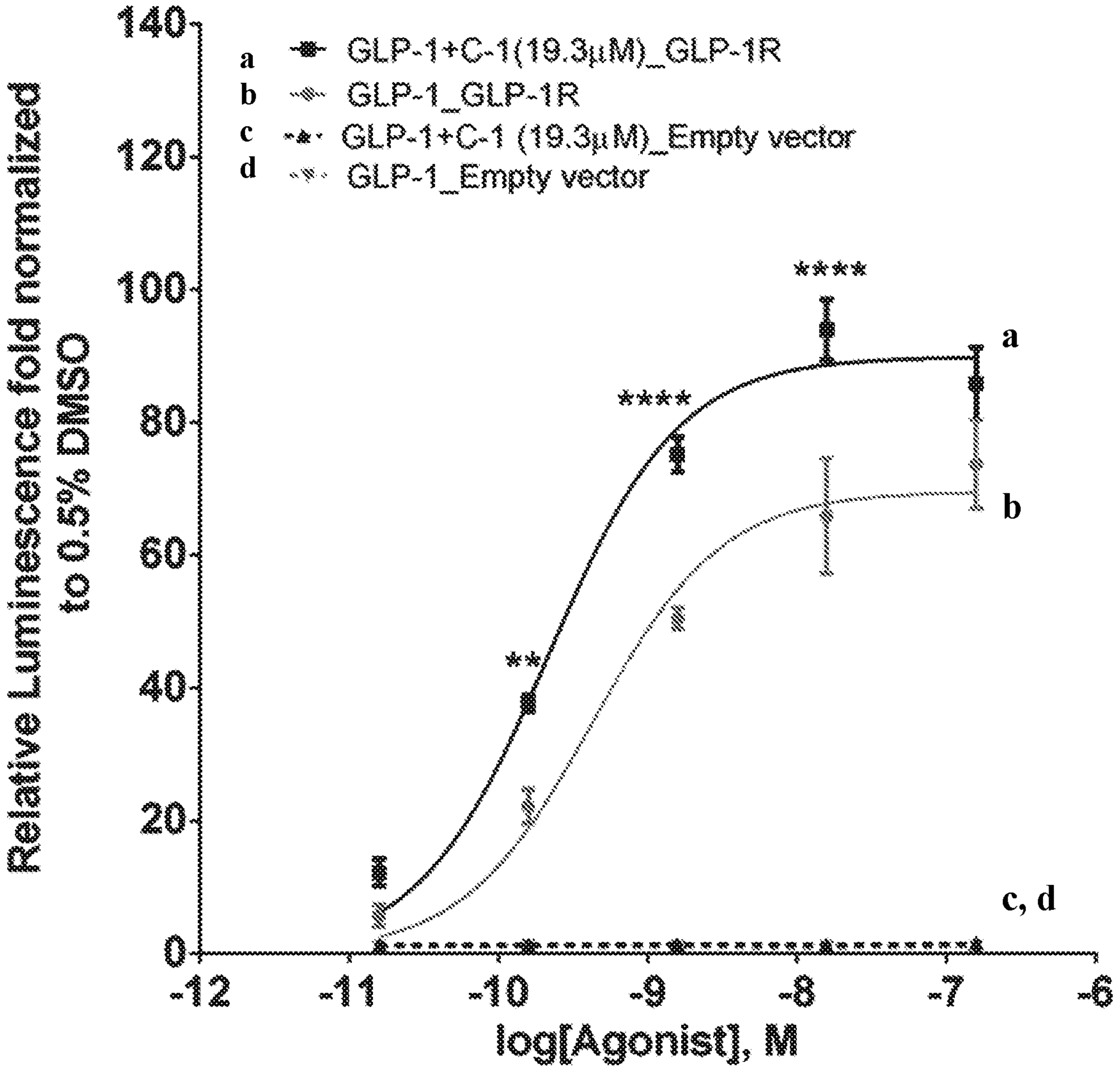
FIG. 3 is a graph showing allosteric effect of Compound Ia on GLP-1R. The effect of GLP-1 on HEK293 cells expressing human GLP-1R or empty vector in the presence or absence of Compound Ia (19.3 μM). GLP-1R activation was assessed as luminescence normalized to protein concentration and plotted as luminescence fold change with respect to vehicle control (0.5% DMSO). Data are average of three independent experiments with at least three technical replicates for each conditions and error bars for each concentration were plotted as SEM (n=3). Statistical analysis was done using 2-way ANOVA (**p<0.0001; p<0.001).

Example 1: Small-Molecule Agonists of GLP-1R Identified Through in Silico Screening The cryo-EM structure of GLP-1R (PDB ID: 5VAI), which showed the active state of the 7TM, was adopted for in silico screening. Through SiteFinder analysis in MOE, a number of potential ligand binding sites on this structure were predicted (Table 1). Among them, the largest predicted site is the orthosteric GLP-1 binding site, and the second largest site located far from the orthosteric site in the 7TM partially overlaps with known allosteric sites in GLP-1R (FIGS. 9A-9D). This site was thus regarded as a potential allosteric site and chosen for in silico screening. A total of 5,689 compounds that have similar ligand properties (molecular weight, x log P, hydrogen donors, hydrogen acceptor and polar surface area) to that of 23 known GLP-1R agonists were identified through compound similarity search. Using the Glide SP docking mode from the Schrodinger Suite first, those 5,689 compounds were docked into the predicted allosteric site on the 7TM of GLP-1R. Glide in the Schrodinger Suite is one of the best docking tools to identify potential protein effectors. Based on their docking scores, the top 16 ranked compounds were chosen for re-docking using the Glide XP mode and then the Induced Fit Docking (IFD). Top ranked poses were visually inspected and as expected they all bound to the proposed allosteric site in GLP-1R (FIG. 1A). Among the top 10 ranked compounds, the one with small molecular weight and the smallest x log P (octanol/water) (Ia) was purchased and experimentally tested for its potential activity against GLP-1R (Table 2). In vitro activity of the selected compound Ia (Table 2) was first studied using human GLP-1R dependent luciferase reporter system. In this screening system, the activation of the human GLP-1R was measured as the amount of luminescence in response to cyclic adenosine monophosphate (cAMP), which in turn was normalized to the amount of protein. Negative control was included in all experiments to evaluate non-specific effect of the compound (if any). From in vitro studies, Ia was found to activate human GLP-1R and its $EC_{50}$ value was determined as 21 μM (FIG. 2). Low level and decreased response of GLP-1 have been observed in some Type 2 patients. Therefore, it will be of interest to determine whether compound Ia can act as a positive allosteric modulator (PAM) of GLP-1R and enhance the affinity and efficacy of endogenous GLP-1. The activation of GLP-1R by different concentrations of GLP-1 (0.014 nM-145 nM) in combination with Ia (19.3 μM) was studied by luciferase activity responding to CAMP production using HEK293-CREB cells transiently expressing human GLP-1R. The GLP-1R activity stimulated by GLP-1 in combination with Ia (19.3 μM) was significantly increased than using GLP-1 alone and the allosteric effect was found to be dose dependent (FIG. 3). Overall, the $EC_{30}$ of GLP-1 was decreased from $1.5\times10^{-10}$M for GLP-1 alone to $0.8\times10^{-10}$M for GLP-1 in combination with Ia (19.3 μM); and the efficacy of GLP-1 was increased from 74.4=5.3 fold for GLP-1 alone to 92.0±3.5 fold for GLP-1 in the presence of Ia (19.3 μM). These dose response analyses suggested that Ia also acted as a PAM of human GLP-1R.

Figure 4:
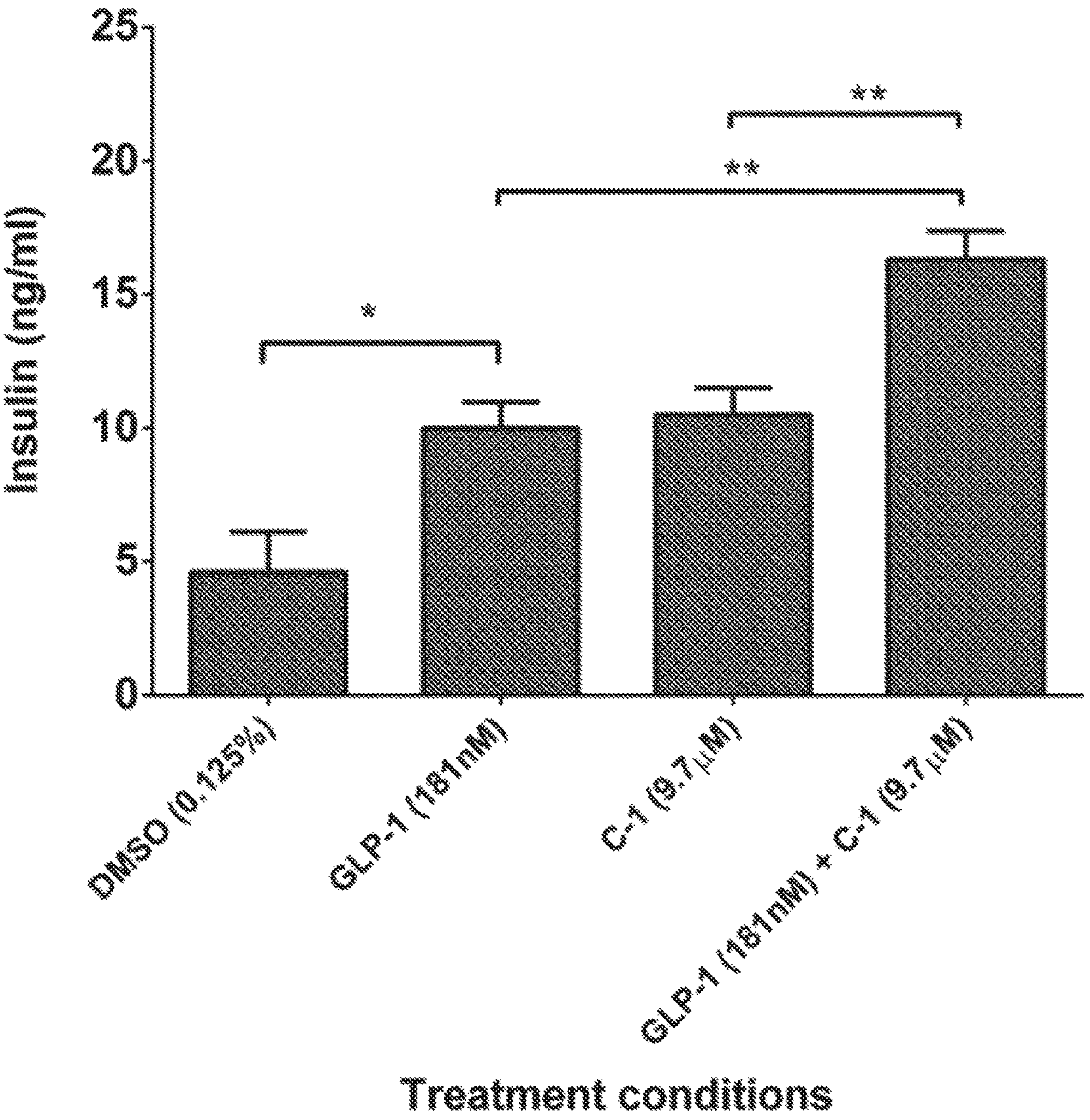
FIG. 4 is a graph showing glucose stimulated insulin production induced by GLP-1 and Compound Ia in INS-1 832/13 cells. INS-1 832/13 cells were treated with GLP-1 (0.18 μM) and Compound Ia (9.7 μM) in the presence of 16.7 mM glucose after 2 hours of starvation with KRB buffer. Data are average of three independent experiments and error bars for each concentration were plotted as SEM (n=3).

In certain embodiments, the invention provides small molecule PAMs of GLP-1R that stimulate insulin production in pancreatic β cells. The insulin production activity of Ia was assessed by in vitro insulin secretion assay in INS-1 832/13 cells. The results indicated that, like GLP-1, Ia can stimulate insulin secretion in the presence of 16.7 mM of glucose and the insulin production by GLP-1 and Ia was more than two-fold compared to vehicle control at both time points (FIG. 4). In addition, no significant difference was observed between the amount of insulin produced by GLP-1 and Ia. However, the amount of insulin produced by GLP-1 in combination with Ia was more than that produced by GLP-1 and Ia, respectively. These data indicated that Ia can induce glucose-dependent insulin production in GLP-1R expressed cells as well as improve GLP-1's efficacy.

TABLE 1

List of putative ligand binding sites present in 7TM of GLP-1R using Site Finder module in MOE.

| No. | Size | PLB | Hyd | Side | Residues |
|---|---|---|---|---|---|
| 1 | 239 | 3.39 | 78 | 133 | Thr29 Ser135 Glu138 Glu139 Leu142 Ser143 Tyr145 Ile146 Thr149 Tyr152 Arg190 Val194 Lys197 Asp198 Leu201 Lys202 Met204 Tyr205 Phe230 Met233 Gln234 Val237 Tyr241 Trp284 Glu294 Cys296 Trp297 Thr298 Arg299 Asn300 Ser301 Trp306 Ile309 Arg310 Ile313 Leu314 Ile317 Glu364 Phe367 Val370 Ala375 Arg376 Gly377 Phe381 Leu384 Glu387 Leu388 Thr391 |
| 2 | 67 | 0.41 | 29 | 54 | Arg176 Asn177 Ile179 His180 Glu247 Tyr250 Leu251 Leu254 Leu255 Val327 Val331 Ser352 Thr353 Thr355 Leu356 Leu359 Leu401 Tyr402 Val405 Asn406 Glu408 |
| 3 | 16 | −0.19 | 2 | 9 | Met204 Asp215 Gly216 Leu217 Ser219 Tyr220 Asp222 Ser223 Cys226 Gly295 Cys296 |
| 4 | 5 | −0.30 | 3 | 9 | Ala200 Trp203 Asp222 Gly225 Cys226 Val229 |
| 5 | 8 | −0.30 | 11 | 16 | Ile165 Phe169 Phe413 Ser416 Trp417 Trp420 |
| 6 | 6 | −0.33 | 9 | 15 | Val332 Leu335 Lys336 Met340 Lys346 |
| 7 | 5 | −0.34 | 10 | 12 | Thr175 Tyr178 Gln263 Phe266 Lys267 |
| 8 | 6 | −0.36 | 12 | 16 | Lys351 Leu354 Thr355 Ile357 Pro358 Phe390 Leu401 |
| 9 | 9 | −0.36 | 11 | 11 | Leu228 Val229 Leu231 Leu232 Ile282 |
| 10 | 3 | −0.40 | 10 | 11 | Ile147 Tyr148 Val150 Gly151 Phe393 |
| 11 | 11 | −0.40 | 8 | 8 | Ala158 Ile161 Ala162 Ile165 Phe404 Phe413 |
| 12 | 10 | −0.40 | 13 | 15 | Tyr242 Leu245 Ile272 Val276 Pro312 Phe315 Ala316 |
| 13 | 8 | −0.41 | 5 | 7 | Arg264 Lys267 Leu268 Ser271 |

TABLE 2

Top ranked compounds in the predicted allosteric binding site of GLP-1R with their docking scores.

| No. | ZINC ID | Molecular Weight | xlogP (octanol/water) | IFD Score |
|---|---|---|---|---|
| 1 | ZINC00664155 | 469.483 | 5.367 | −12.791 |
| 2 | ZINC02131898 | 419.263 | 5.168 | −12.689 |
| 3 | ZINC00707027 | 423.470 | 5.280 | −11.661 |
| 4 | ZINC00381912 | 334.460 | 5.117 | −11.327 |
| 5 | ZINC02057087 | 344.455 | 4.687 | −10.891 |
| 6 | ZINC08385113 | 435.463 | 5.126 | −10.86 |
| 7 | ZINC08407873 | 477.586 | 6.217 | −10.748 |
| 8 | ZINC08430153 | 439.959 | 6.610 | −10.719 |
| 9 | ZINC19797057 (C-1) | 399.525 | 3.897 | −10.265 |
| 10 | ZINC05728874 | 407.702 | 5.158 | −9.798 |

Site Specific Mutagenesis Studies Confirms the Proposed Binding Site of Ia in GLP-1R Inspection of the different binding poses of Ia in the proposed binding site generated from Glide XP and IFD docking indicated that Ia forms hydrogen bonds with side chains of residues N406 and S352 (FIG. 1A). Therefore, these two amino acids were chosen for site-specific mutagenesis studies to confirm the proposed binding site. N406A and S352A GLP-1R mutants were generated by traditional PCR method and confirmed by sequencing. In addition, V332W was chosen as the negative control for Ia binding. V332 is not in the predicted binding site for Ia, but it is one of the residues that was suggested being involved in the binding of Compound 2.

Figure 5A:
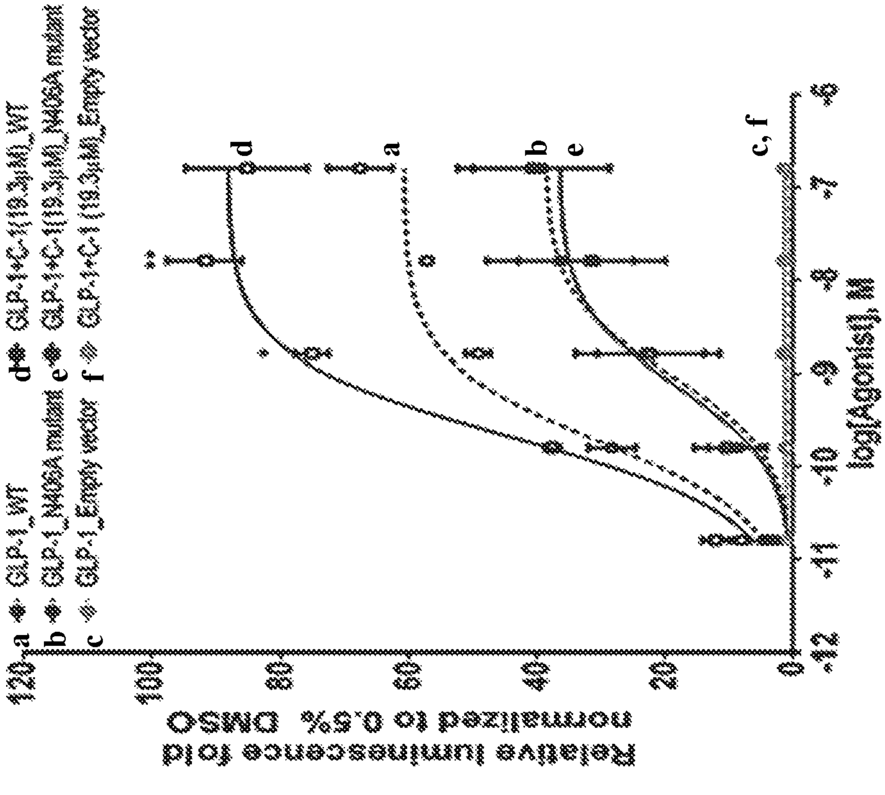
FIGS. 5A-5C are graphs related to site-specific mutagenesis studies on human GLP-1R.
Figure 5B:
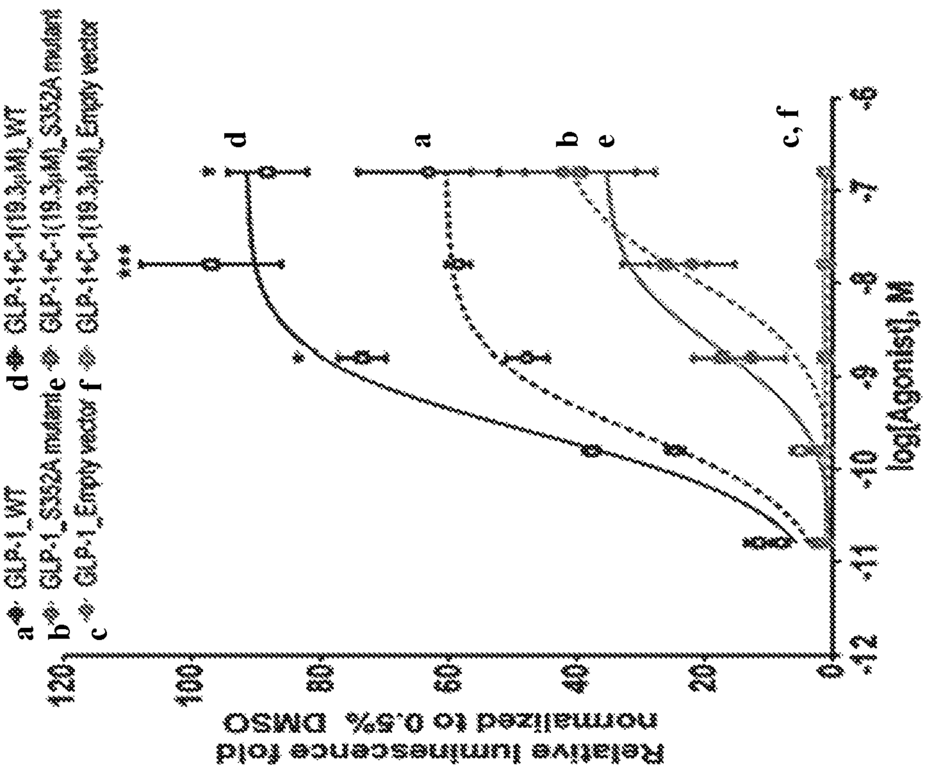
Figure 5C:
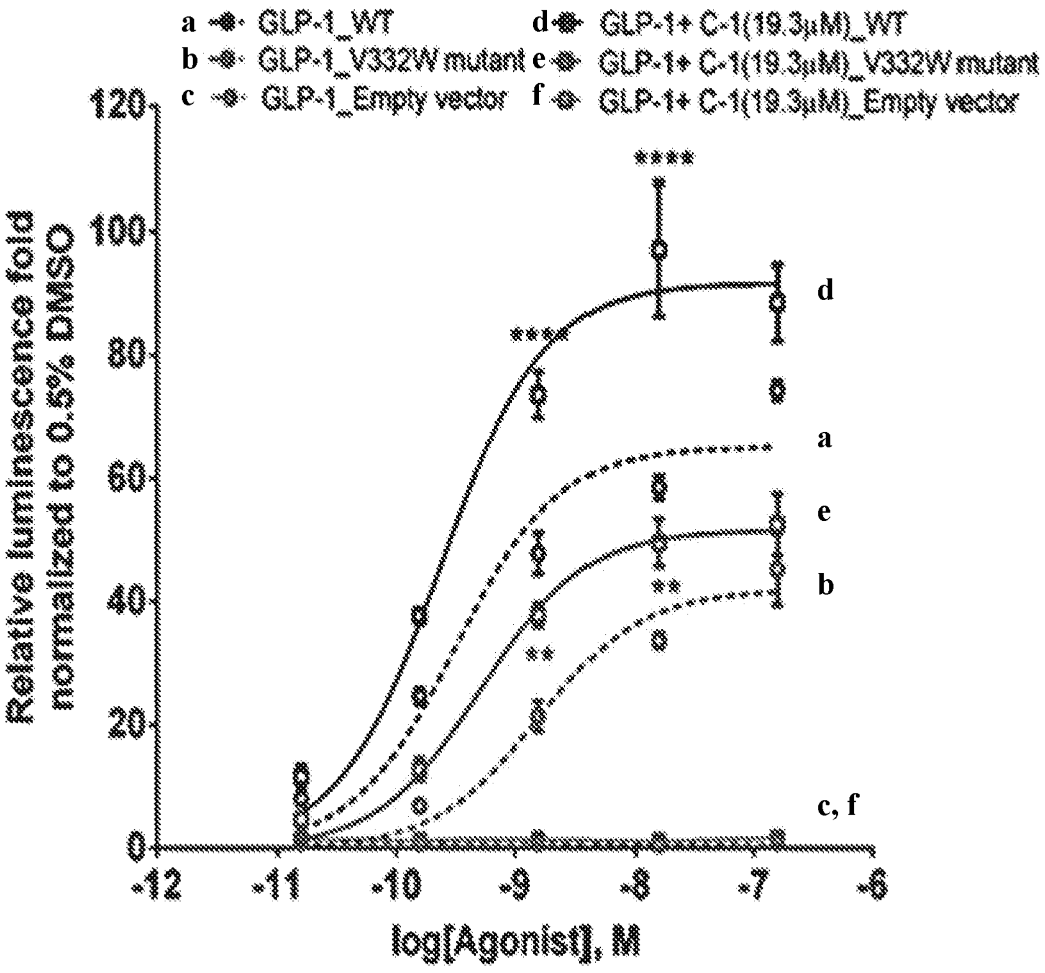
Figure 6A:
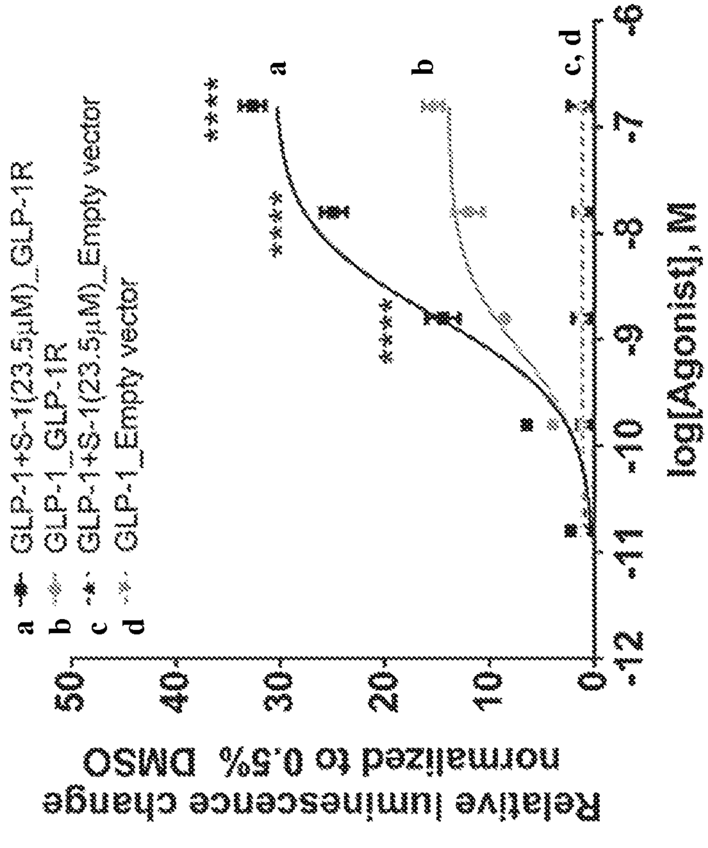
FIGS. 6A-6B comprise graphs showing allosteric effect of Compound Ib (S-1; also known as ethyl 2-amino-7-methyl-4,5,6,7-tetrahydrobenzo[b]thiophene-3-carboxylate) and Compound Ic (S-2; also known as 3-amino-2-mercapto-8-methyl-5,6,7,8-tetrahydrobenzo[4,5]thieno[2,3-d]pyrimidin-4(3H)-one) on human GLP-1R.
Figure 6B:
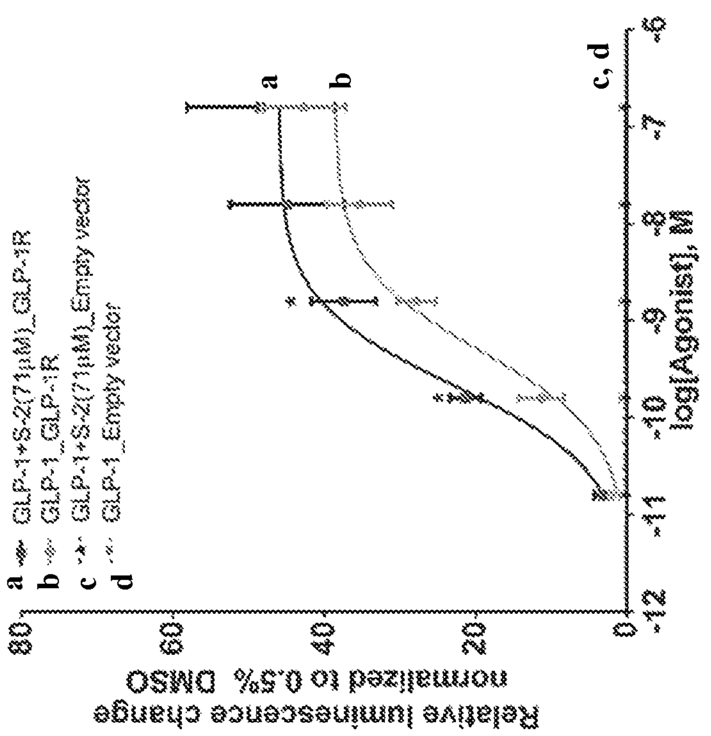

To study the potential change in the allosteric activity of Ia on GLP-1R mutants N406A, S352A and V332W individually, the effect of GLP-1 (0.014 nM-145 nM) in combination with Ia (19.3 μM) was compared between WT and mutant GLP-1R transfected HEK-CREB luciferase cell line using luciferase assay. While the WT GLP-1R activity stimulated by GLP-1 in combination with Ia (19.3 μM) was significantly increased than using GLP-1 alone and the allosteric effect was dose dependent, the N406A and S352A mutant GLP-1R activity stimulated by GLP-1 in combination with Ia (19.3 μM) remained the same, as using GLP-1 alone and the allosteric effect was not observed (FIG. 5A-5C). These results suggested that either N406A or S352A mutation abolished the allosteric effect of Ia and as a result the GLP-1's affinity and efficacy was not impacted in the presence of Ia. Without wishing to be limited by any theory, this is likely due to the fact that both mutations have disrupted the hydrogen bond interactions between N406 or S352 and Ia, which affected the binding of Ia in the proposed pocket and subsequently abolished its allosteric activity on GLP-1R. Consistently, V332W mutation had no effect on the allosteric activity of Ia, suggesting that Ia does not bind to other sites other than the proposed one.

Optimization of Ia Through Structure-Based Molecule Design

Figure 10A:
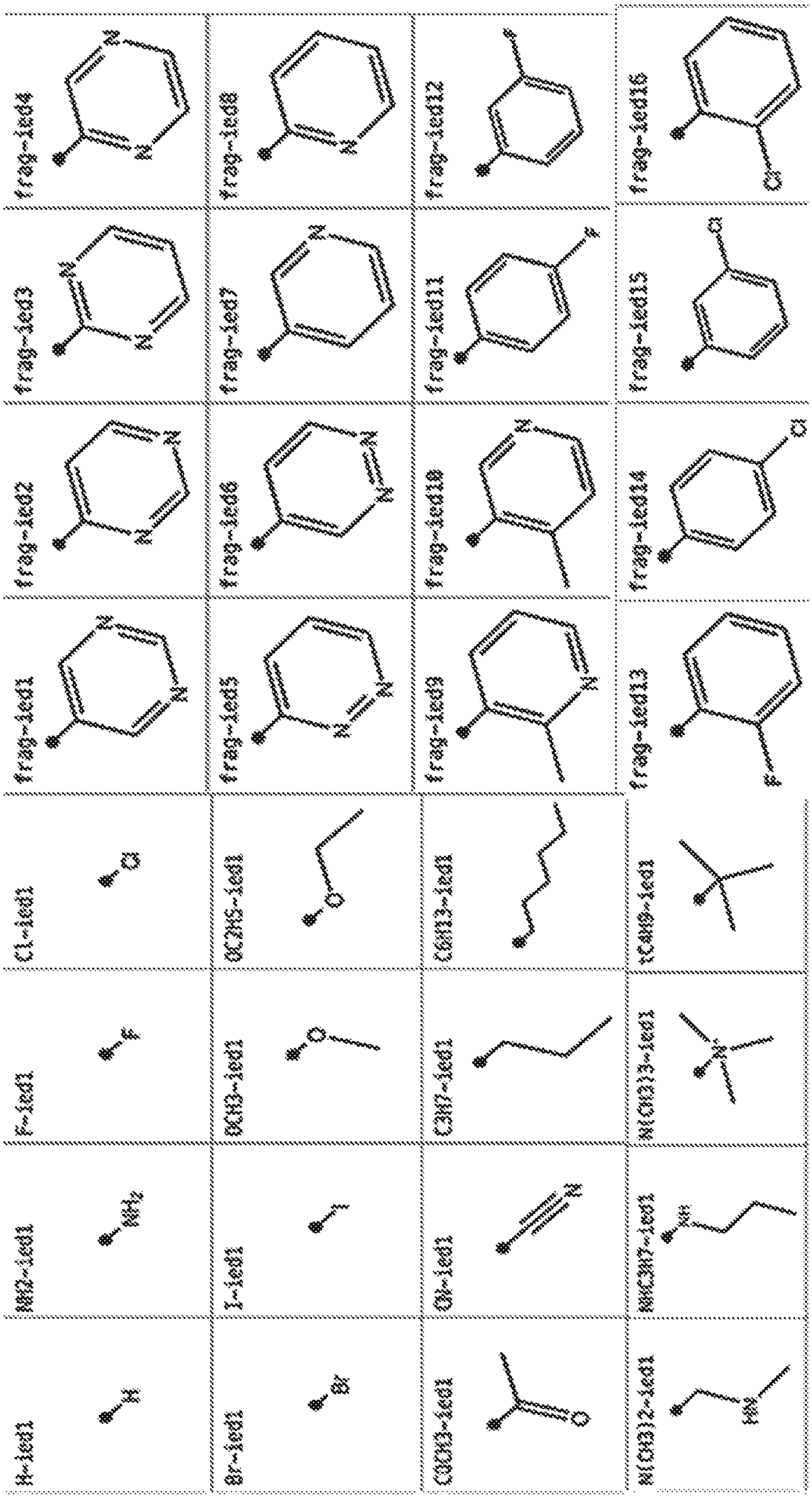
FIGS. 10A-10B show a list of substituent groups used to modify and optimize Compound Ia. R-groups generated using Interactive Enumeration module of Schrodinger Suite and used to modify the C-1 (Compound Ia) scaffold.
Figure 10B:
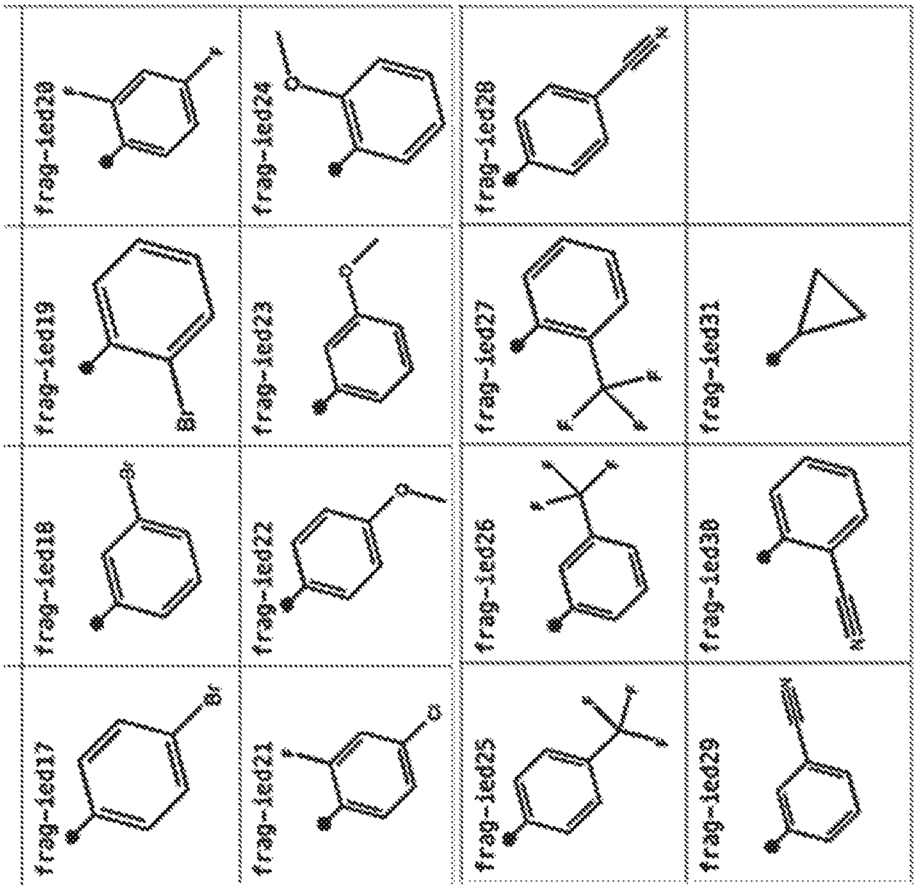
Figure 10B:
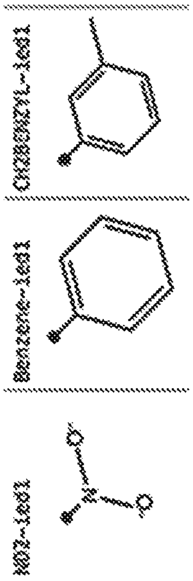
Figure 11:
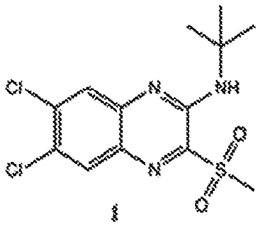
FIG. 11 shows structures of reported GLP-1R PAMs and ago-PAMs. 1. Compound 2; 2, BETP; 3, Quercetin; 4, T0506-3445; 5, VU0056556; 6, (S)-8 (enantiomer of compound 8 in Morris, et al., 2014, Journal of Medicinal Chemistry 57 (23): 10192-10197); 7, VU0453379; 8, M-4.
Figure 11:
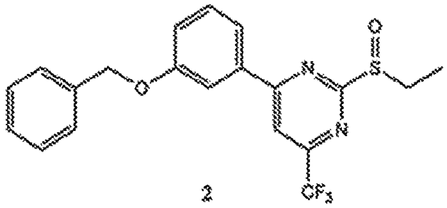
Figure 11:
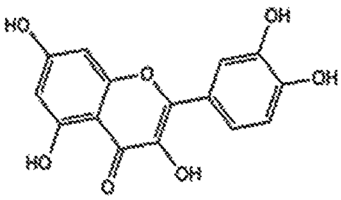
Figure 11:
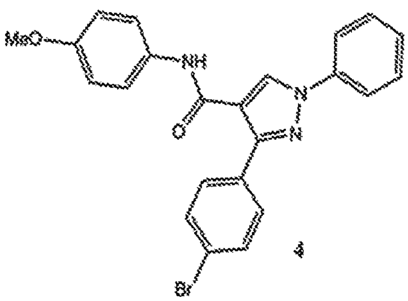
Figure 11:
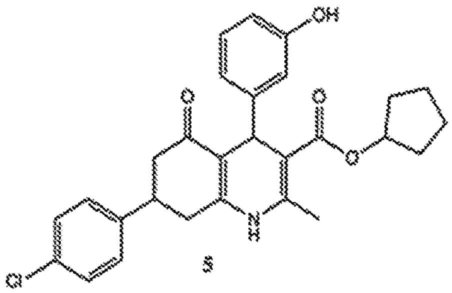
Figure 11:
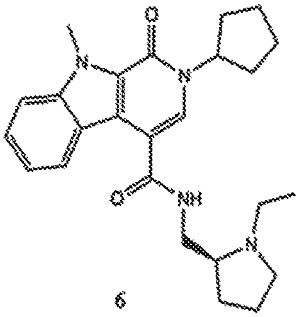
Figure 11:
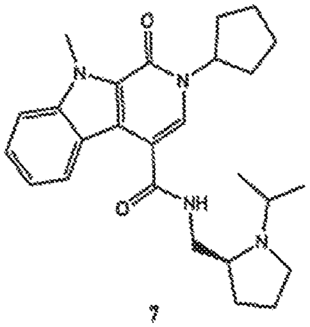
Figure 11:
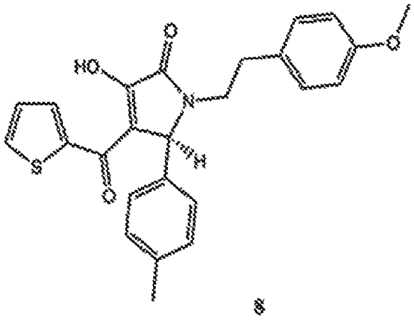

After the confirmation of the allosteric activity of Ia as well as its binding site on GLP-1R, Ia was further modified to improve its binding affinity. The modification was performed in two steps. In Step One, the H-atoms at different positions of Ia (FIG. 1B) were systematically replaced with various functional groups (FIG. 10) while the interactions with N406 and S352 were not affected. In Step Two, modified compounds generated in the first step were docked into the same binding site as described previously to identify the compounds with the small molecular weight and highest docking scores (Table 3). Based on the structure of top ranked compounds and their synthetic feasibility, four compounds with the same scaffold was eventually synthesized following the route in Scheme 1 and all intermediates and the final product were tested in vitro for their allosteric activity on human GLP-1R using luciferase based reporter gene system. Of the three intermediate and one final product of the Ia modified compound, two intermediates (10, S-1 and 12, Ic) were found to be the PAMs of GLP-1R (FIG. 7). The activation of GLP-1R by different concentrations of GLP-1 (0.014 nM-145 nM) in combination with Ib (23.5 μM) and Ic (71 μM) respectively was studied by luciferase activity responding to CAMP production using HEK293-CREB cells transiently expressing human GLP-1R. GLP-1R activity stimulated by GLP-1 in combination with Ib (23.5 μM) and Ic (71 μM) respectively was significantly increased than using GLP-1 alone and the allosteric effect was dose dependent (FIG. 7).

Scheme 1.

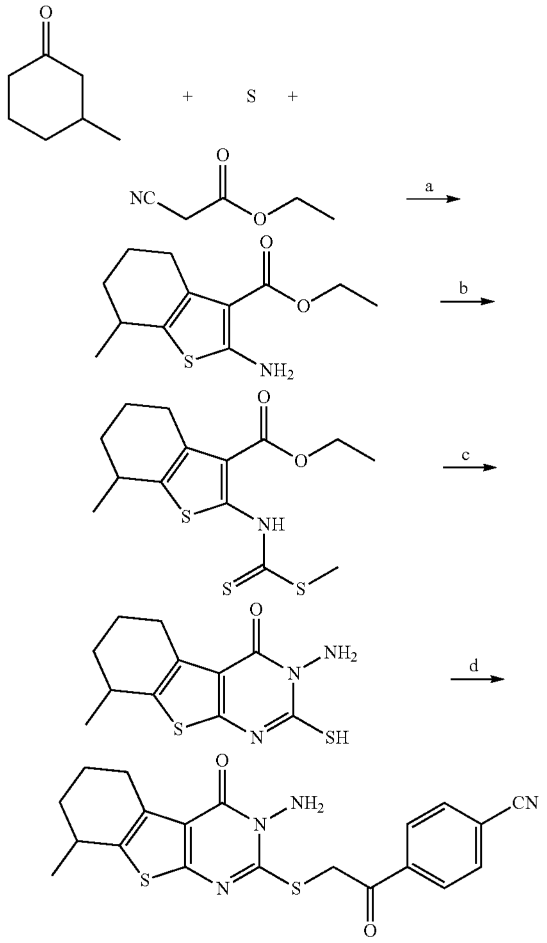

General synthetic scheme for substituted 3-amino-8-methyl-2-((2-oxo-2-phenylethyl)thio)-5,6,7,8-tetrahydrobenzo[4,5]thieno[2,3-d]pyrimidin-4(3H)-one. Reagents and conditions: (a) DEA, EtOH, 25° C.; (b) NaOH, $CS_2$, DMS, DMSO, 25° C., 12 hr; (c) hydrazine hydrate (50-60%), MeOH, 25° C., 8 hr; (d) substituted 2-bromo-1-phenylethan-1-one, MeOH, reflux, 8 hr.

TABLE 3

Top ranked compounds generated through functional group addition with their docking scores.

| No | Compound | MW | IFD Score |
|---|---|---|---|
| 1 | C1 | 399.53 | −10.636 |
| 2 | C1; [Berizene]-pos8 | 475.63 | −10.418 |
| 3 | C1; [C6H13]-pos5 | 483.69 | −11.109 |
| 4 | C1; [C6H13]-pos5 | 483.69 | −11.109 |
| 5 | C1; [CH2BENZYL]-pos4; [NH2]-pos5; [I]-pos6 | 630.56 | −10.248 |
| 6 | C1; [CN]-pos2 | 424.54 | −11.681 |
| 7 | C1; [CN]-pos7 | 424.54 | −11.239 |
| 8 | C1; [COCH3]-pos4 | 441.57 | −11.401 |
| 9 | C1; [COCH3]-pos4 | 441.57 | −11.401 |
| 10 | C1; [F]-pos8 | 417.52 | −12.112 |
| 11 | C1; [NO2]-pos4; [C6H13]-pos5; [C6H13]-pos6 | 612.58 | −12.391 |
| 17 | C1; [NO2]-pos4; [NH2]-pos5; [Br]-pos6 | 538.44 | −9.632 |
| 13 | C1; [NO2]-pos4 | 444.53 | −9.863 |
| 14 | C1; [NO2]-pos7 | 444.53 | −11.239 |
| 15 | C1; [NO2]-pos7 | 444.53 | −10.04 |
| 16 | C1; [NO2]-pos7 | 444.53 | −10.04 |
| 17 | C1; [NO2]-pos8 | 444.53 | −10.558 |
| 18 | C1; [NO2]-pos4; [NH2]-pos7; [I]-pos6 | 585.44 | −11.507 |

TABLE 3-continued

Top ranked compounds generated through functional group addition with their docking scores.

| No | Compound | MW | IFD Score |
|---|---|---|---|
| 19 | C1; [NO2]-pos4; [NHC3H7]-pos 7; [Cl]-pos6 | 536.07 | −9.329 |
| 20 | C1; [OCH3]-pos4 | 429.56 | −11.146 |
| 21 | C1; [OCH3-]-pos4 | 429.56 | −11.146 |

Compound Ib Does Not Stimulate VIPR1 Activity

Both Ia binding residues N406 and S352 are conserved in Class B GPCRs, implicating that compound Ib and Ic could bind to other Class B GPCRs. Besides GLP-1R, the HEK293 cells are known to express other functional Class B GPCRs including Vasoactive Intestinal Peptide Receptor 1 (VIPR1)27. Since compound Ic is unstable and less potent, the behavior of Ib (23.5 μM) on VIPR1 in the presence of VIPR peptide agonist (0.014 nM-145 nM) was studied using the same cell line with overexpressed VIPR1. The VIPR1 activity in response to VIPR agonist in combination with Ib was similar to that using VIPR agonist alone, indicating that Ib showed no potential non-specific activity on VIPR1 (FIG. 7).

Ib Stimulates Insulin Secretion

Figure 8:
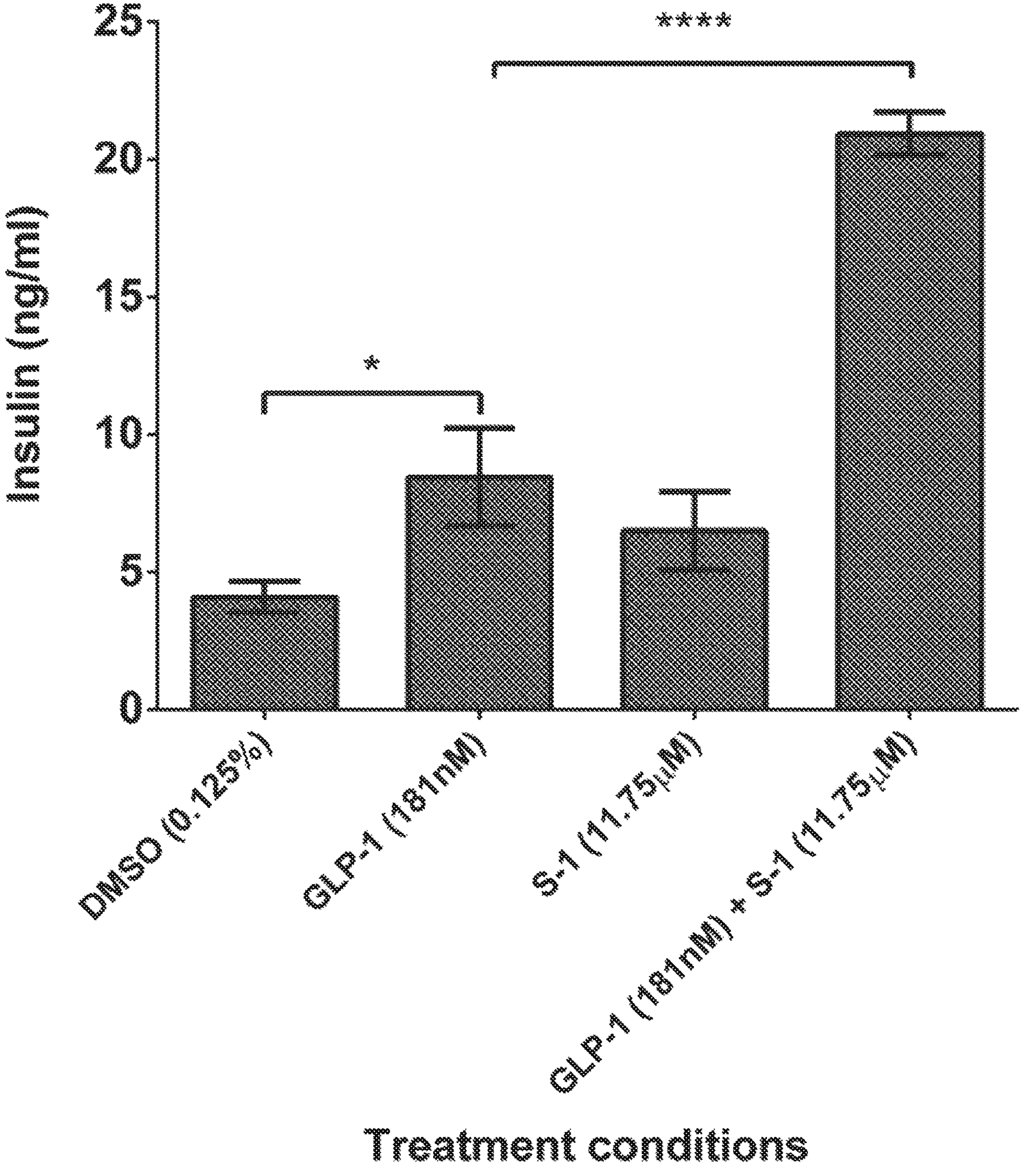
FIG. 8 is a graph showing glucose-stimulated insulin production induced by GLP-1 and Compound Ib (S-1) in INS-1 832/13 cells. INS-1 832/13 cells were treated with GLP-1 (0.18 μM) and Compound Ib (11.75 μM) in the presence of 16.7 mM glucose after 2 hours of starvation with KRB buffer. Data are average of two independent experiments with 3 technical replicates and error bars for each concentration were plotted as SEM (n=3).
Figure 9D:
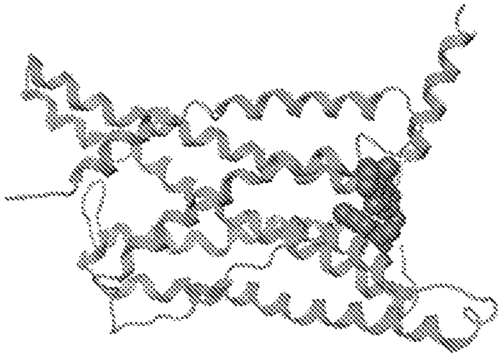
FIGS. 9A-9D illustrate allosteric binding site on GLP-1R.
Figure 9C:
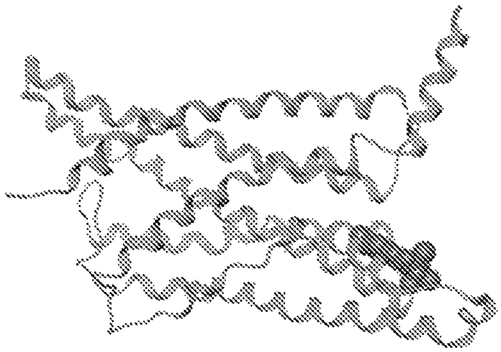
Figure 9B:
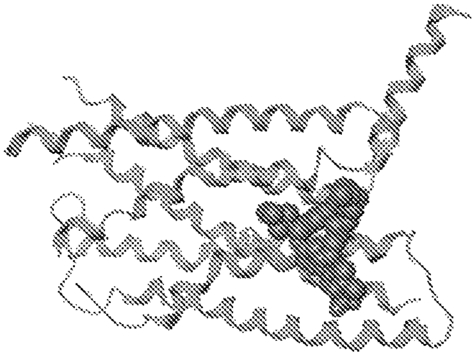
Figure 9A:
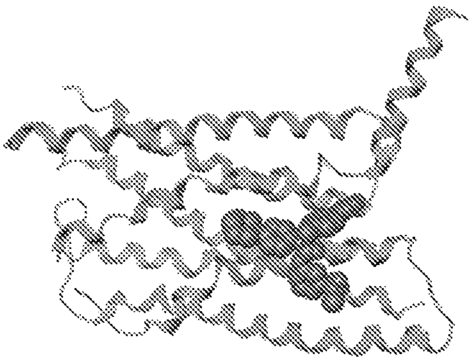

The insulin production activity of Ib was assessed by in vitro insulin secretion assay in INS-1 832/13 cells. The results indicated that no significant difference was observed between the amount of insulin produced by vehicle control and Ib. However, when used in combination with GLP-1, compound Ib can stimulate insulin secretion more than 2.5 fold than GLP-1 alone in the presence of 16.7 mM of glucose (FIG. 8). These data indicated that Ib can enhance glucose-dependent insulin production in GLP-1R expressed cells and might improve GLP-1's efficacy with potential clinical application.

Enumerated Embodiments

The following exemplary embodiments are provided, the numbering of which is not to be construed as designating levels of importance.

Embodiment 1 provides a compound of Formula (I), or a salt, solvate, stereoisomer, geometric isomer, and/or tautomer thereof:

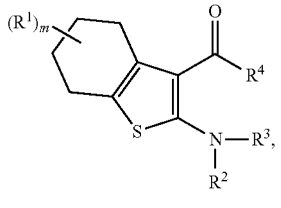

(I)

wherein:

each occurrence of $R^1$ is independently selected from the group consisting of H, halogen, —OH, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ aminoalkyl, optionally substituted $C_1$-$C_6$ haloalkoxy, and optionally substituted $C_1$-$C_6$ haloalkyl;

m is 0, 1, 2, 3, 4, 5, 6, 7, or 8;

each occurrence of $R^2$ and $R^3$ is independently selected from the group consisting of H, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ aminoalkyl, optionally substituted $C_1$-$C_6$ haloalkoxy, and optionally substituted $C_1$-$C_6$ haloalkyl;

$R^4$ is selected from the group consisting of —$NH_2$, —NH($C_1$-$C_6$ alkyl), —N($C_1$-$C_6$ alkyl)($C_1$-$C_6$ alkyl), optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ aminoalkyl, optionally substituted $C_1$-$C_6$ haloalkoxy, and optionally substituted $C_1$-$C_6$ haloalkyl, or $R^2$ is absent and $R^3$ and $R^4$ combine with ═C(XR')—N(R")—* to form a ring, wherein the bond marked as * is with the carbonyl group in the compound; X is selected from the group consisting of O, S, and NR;

each occurrence of R' is independently selected from the group consisting of H, optionally substituted $C_1$-$C_6$ alkyl, optionally substituted $C_3$-$C_8$ cycloalkyl, optionally substituted aryl, optionally substituted —C(═O)-aryl, optionally substituted —C(═O)-heteroaryl, optionally substituted heteroaryl, $(CH_2)_nC(═O)R^5$, and $(CH_2CH_2O)_nC(═O)R^5$, wherein each n is independently an integer from 1 to 10;

each occurrence of $R^5$ is independently optionally substituted $C_3$-$C_8$ cycloalkyl, optionally substituted aryl, or optionally substituted heteroaryl;

each occurrence of R" is independently selected from the group consisting of hydrogen, —NHR, —$N(R)_2$, —$NH_2$, —NH($C_1$-$C_6$ alkyl), and —N($C_1$-$C_6$ alkyl)($C_1$-$C_6$ alkyl); and each occurrence of R is independently selected from the group consisting of hydrogen, $C_1$-$C_6$ alkyl, $C_3$-$C_8$ cycloalkyl, and phenyl.

Embodiment 2 provides the compound of Embodiment 1, wherein R' is

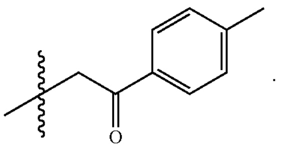 [SMILES: *CC(=O)c1ccc(C)cc1]

Embodiment 3 provides the compound of any of Embodiments 1-2, wherein X is S.

Embodiment 4 provides the compound of any of Embodiments 1-3, which is a compound of Formula (II):

(II)

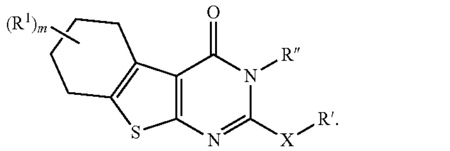

Embodiment 5 provides the compound of any of Embodiments 1-4, wherein one, and/or at least one, occurrence of $R^1$ is $C_1$-$C_6$ alkyl.

Embodiment 6 provides the compound of any of Embodiments 1-5, wherein one, and/or at least one, occurrence of $R^1$ is methyl, ethyl, n-propyl, isopropyl, n-butyl, isobutyl, sec-butyl, and/or t-butyl.

Embodiment 7 provides the compound of any of Embodiments 1 and 5-6, wherein $R^4$ is optionally substituted $C_1$-$C_6$ alkoxy.

Embodiment 8 provides the compound of any of Embodiments 1 and 5-7, wherein $R^4$ is optionally substituted methoxy, optionally substituted ethoxy, optionally substituted n-propoxy, optionally substituted isopropoxy, optionally substituted n-butoxy, optionally substituted isobutoxy, optionally substituted sec-butoxy, or optionally substituted t-butoxy.

Embodiment 9 provides the compound of any of Embodiments 1-8, which is one of the following:

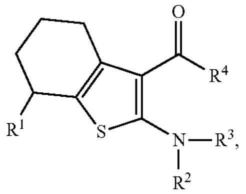

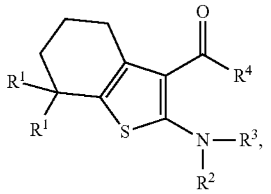

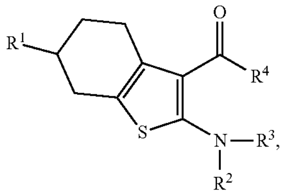

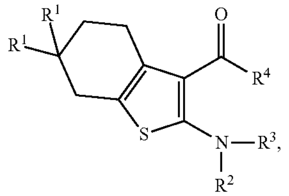

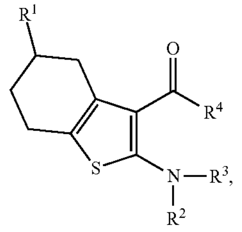

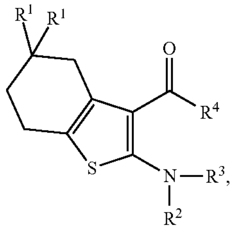

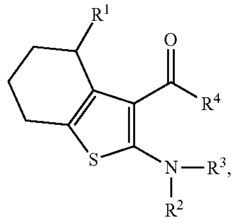

or

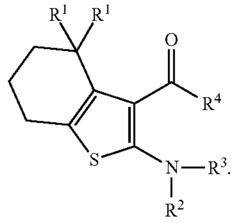

Embodiment 10 provides the compound of any of Embodiments 1-9, which is selected from the group consisting of

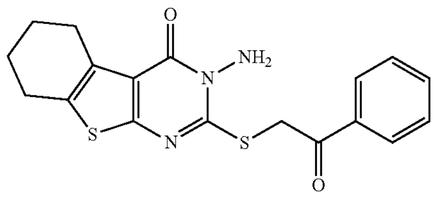 [SMILES: Nn1c(SCC(=O)c2ccccc2)nc2sc3c(c2c1=O)CCCC3]

3-amino-2-((2-oxo-2-phenylethyl)thio)-5,6,7,8-tetrahydrobenzo[4,5]thieno[2,3-d]pyrimidin-4(3H)-one,

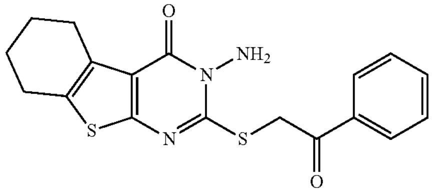 [SMILES: Nn1c(SCC(=O)c2ccccc2)nc2sc3c(c2c1=O)CCCC3]

3-amino-5-methyl-2-((2-oxo-2-(p-tolyl)ethyl)thio)-5,6,7,8-tetrahydrobenzo[4,5]thieno[2,3-d]pyrimidin-4(3H)-one,

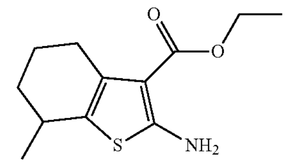 [SMILES: CCOC(=O)c1c(N)sc2c1CCCC2C]

ethyl 2-amino-7-methyl-4,5,6,7-tetrahydrobenzo[b]thiophene-3-carboxylate,

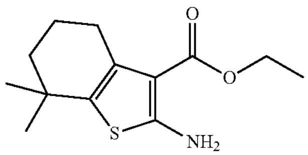

ethyl 2-amino-7,7-dimethyl-4,5,6,7-tetrahydrobenzo[b]thiophene-3-carboxylate,

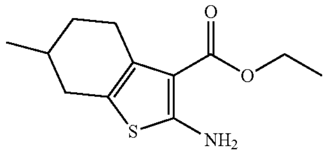 [SMILES: CCOC(=O)c1c(N)sc2c1CCC(C)C2]

ethyl 2-amino-6-methyl-4,5,6,7-tetrahydrobenzo[b]thiophene-3-carboxylate,

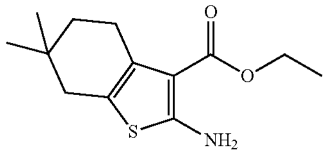

ethyl 2-amino-6,6-dimethyl-4,5,6,7-tetrahydrobenzo[b]thiophene-3-carboxylate,

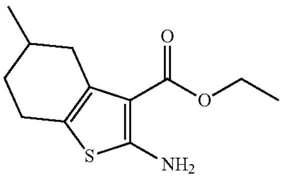

ethyl 2-amino-5-methyl-4,5,6,7-tetrahydrobenzo[b]thiophene-3-carboxylate,

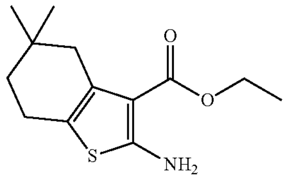 [SMILES: CCOC(=O)c1c(N)sc2c1CC(C)(C)CC2]

ethyl 2-amino-5,5-dimethyl-4,5,6,7-tetrahydrobenzo[b]thiophene-3-carboxylate,

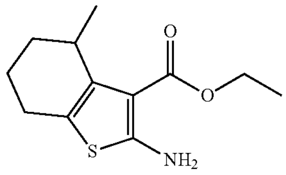 [SMILES: CCOC(=O)c1c(N)sc2c1C(C)CCC2]

ethyl 2-amino-4-methyl-4,5,6,7-tetrahydrobenzo[b]thiophene-3-carboxylate,

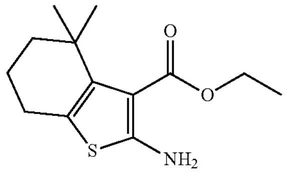 [SMILES: CCOC(=O)c1c(N)sc2c1C(C)(C)CCC2]

ethyl 2-amino-4,4-dimethyl-4,5,6,7-tetrahydrobenzo[b]thiophene-3-carboxylate, and

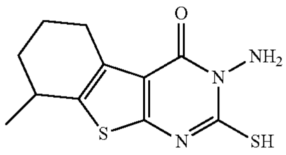 [SMILES: CC1CCCc2c1sc1nc(S)n(N)c(=O)c21]

3-amino-2-mercapto-8-methyl-5,6,7,8-tetrahydrobenzo[4,5]thieno[2,3-d]pyrimidin-4(3H)-one.

Embodiment 11 provides the compound of any of Embodiments 1-10, wherein the compound is a Glucagon-like peptide 1 receptor (GLP-1R) agonist.

Embodiment 12 provides the compound of any of Embodiments 1-11, wherein the compound is a positive allosteric modulator (PAM) of GLP-1R.

Embodiment 13 provides the compound of any of Embodiments 1-12, wherein the compound selectively enhances GLP-1R activity.

Embodiment 14 provides the compound of any of Embodiments 1-13, wherein the compound has no significant effect on the activity of other G-protein-coupled receptors (GPCRs).

Embodiment 15 provides a pharmaceutical composition comprising at least one pharmaceutically acceptable carrier and at least one compound of any of Embodiments 1-14, or a salt, solvate, stereoisomer, geometric isomer, and/or tautomer thereof.

Embodiment 16 provides the composition of Embodiment 15, which is formulated for administration by a route selected from the group consisting of oral, parenteral, transdermal, transmucosal, intravesical, intrapulmonary, intraduodenal, intragastrical, intrathecal, subcutaneous, intramuscular, intradermal, intra-arterial, intravenous, intrabronchial, inhalation, and topical.

Embodiment 17 provides the composition of any one of Embodiments 15-16, further comprising at least one additional agent useful for treating, ameliorating, or preventing diabetes and/or insulin resistance in a subject.

Embodiment 18 provides the composition of Embodiment 17, wherein the at least one additional agent is selected from the group consisting of α-glucosidase inhibitor, lipase inhibitor, sulfonyl urea, meglitinide, biguanide, thiazolidinedione, pramlintide, incretin mimetic, DPP-IV inhibitor, and SGLT2 inhibitor.

Embodiment 19 provides a method of treating, ameliorating, or preventing insulin resistance and/or diabetes in a subject, the method comprising administering to the subject a therapeutically effective amount of the compound of any of Embodiments 1-14, or a salt, solvate, stereoisomer, geometric isomer, and/or tautomer thereof.

Embodiment 20 provides the method of Embodiment 19, wherein the diabetes is type II diabetes.

Embodiment 21 provides the method of any of Embodiments 19-20, wherein the compound is administered as a pharmaceutical composition to the subject.

one additional agent as compared to the dose of the additional agent alone that is required to achieve similar results in treating, ameliorating, or preventing insulin resistance and/or diabetes.

Embodiment 25 provides the method of any of Embodiments 22-24, wherein administering the compound to the subject enhances the activity, and/or reduced at least one side effect, of the at least one additional agent.

Embodiment 26 provides the method of any of Embodiments 22-25, wherein the compound and the at least one additional agent are co-administered to the subject.

Embodiment 27 provides the method of any of Embodiments 22-26, wherein the compound and the at least one additional agent are co-formulated.

Embodiment 28 provides the method of any of Embodiments 19-27, wherein the subject is a mammal.

Embodiment 29 provides the method of Embodiment 28, wherein the subject is a human.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

```
                              SEQUENCE LISTING


<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: Chemically synthesized forward primer

<400> SEQUENCE: 1

ttatactgct ttgtcgccaa tgaggtccag ctg                                33


<210> SEQ ID NO 2
<211> LENGTH: 33
<212> TYPE: DNA
<213> ORGANISM: Artificial Sequence
<220> FEATURE:
<223> OTHER INFORMATION: Chemically synthesized reverse primer

<400> SEQUENCE: 2

cagctggacc tcattggcga caaagcagta taa                                33
```

Embodiment 22 provides the method of any of Embodiments 19-21, wherein the subject is further administered at least one additional agent useful for treating, ameliorating, or preventing diabetes and/or insulin resistance.

Embodiment 23 provides the method of Embodiment 22, wherein the at least one additional agent is selected from the group consisting of α-glucosidase inhibitor, lipase inhibitor, sulfonyl urea, meglitinide, biguanide, thiazolidinedione, pramlintide, incretin mimetic, DPP-IV inhibitor, and SGLT2 inhibitor.

Embodiment 24 provides the method of any of Embodiments 22-23, wherein administering the compound to the subject allows for administering a lower dose of the at least

What is claimed is:

1. A compound of formula:

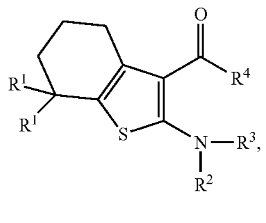

wherein:

each occurrence of $R^1$ is independently selected optionally substituted $C_1$-$C_6$ alkyl;

$R^2$ and $R^3$ are each independently selected from the group consisting of H and optionally substituted $C_1$-$C_6$ alkyl;

$R^4$ is selected from the group consisting of —$NH_2$, —$NH(C_1$-$C_6$ alkyl), —$N(C_1$-$C_6$ alkyl)($C_1$-$C_6$ alkyl), and optionally substituted $C_1$-$C_6$ alkoxy, or $R^2$ is absent and $R^3$ and $R^4$ combine with =C(XR')—N(R")—* to form a ring, wherein the bond marked as * is with the carbonyl group in the compound;

X is selected from the group consisting of O, S, and NR;

R is H;

each occurrence of R' is independently selected from the group consisting of H, optionally substituted $C_1$-$C_6$ alkyl, $(CH_2)_nC(=O)R^5$, and $(CH_2CH_2O)_nC(=O)R^5$, wherein each n is independently 1, 2, 3, 4, 5, 6, 7, 8, 9, or 10;

each occurrence of $R^5$ is independently selected optionally substituted phenyl;

each occurrence of R" is independently selected from the group consisting of hydrogen, —$NH_2$, —$NH(C_1$-$C_6$ alkyl), and —$N(C_1$-$C_6$ alkyl)($C_1$-$C_6$ alkyl);

wherein each optional substituent is independently selected from the group consisting of fluorine, chlorine, bromine, iodine, —CN, —$NH_2$, —OH, —$NH(CH_3)$, —$N(CH_3)_2$, —$CH_3$, —$CH_2CH_3$, —$CH(CH_3)_2$, —$CF_3$, —$CH_2CF_3$, —$OCH_3$, —$OCH_2CH_3$, —$OCH(CH_3)_2$, —$OCF_3$, —$OCH_2CF_3$, —$S(=O)_2$—$CH_3$, —C(=O)$NH_2$, —C(=O)—$NHCH_3$, —NHC(=O)$NHCH_3$, —C(=O)$CH_3$, and —C(=O)OH;

or a salt, solvate, stereoisomer, geometric isomer, or tautomer thereof.

2. The compound of claim 1, wherein R' is

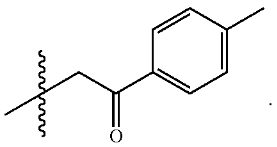 [SMILES: *CC(=O)c1ccc(C)cc1]

.

3. The compound of claim 1, wherein X is S.

4. The compound of claim 1, wherein one, or at least one, occurrence of $R^1$ is $C_1$-$C_6$ alkyl.

5. The compound of claim 1, wherein one, or at least one, occurrence of $R^1$ is methyl, ethyl, n-propyl, isopropyl, n-butyl, isobutyl, sec-butyl, or t-butyl.

6. The compound of claim 1, wherein $R^4$ is optionally substituted $C_1$-$C_6$ alkoxy.

7. The compound of claim 1, wherein $R^4$ is optionally substituted methoxy, optionally substituted ethoxy, optionally substituted n-propoxy, optionally substituted isopropoxy, optionally substituted n-butoxy, optionally substituted isobutoxy, optionally substituted sec-butoxy, or optionally substituted t-butoxy.

8. The compound of claim 1, which is

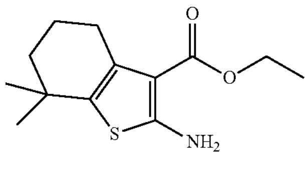 [SMILES: CCOC(=O)c1c(N)sc2c1CCCC2(C)C]

ethyl 2-amino-7,7-dimethyl-4,5,6,7-tetrahydrobenzo[b]thiophene-3-carboxylate.

9. A pharmaceutical composition comprising at least one pharmaceutically acceptable carrier and an effective amount of at least one compound of claim 1, or a salt, solvate, stereoisomer, geometric isomer, or tautomer thereof.

10. The composition of claim 9, further comprising at least one additional agent useful for treating or ameliorating type II diabetes in a subject, wherein the at least one additional agent is selected from the group consisting of an α-glucosidase inhibitor, a lipase inhibitor, a sulfonyl urea, a meglitinide, a biguanide, a thiazolidinedione, pramlintide, incretin mimetic, DPP-IV inhibitor, and SGLT2 inhibitor.

11. The composition of claim 10, wherein at least one of the following applies:

(a) the α-glucosidase inhibitor is selected from the group consisting of acarbose, miglitol, and voglibose;

(b) the lipase inhibitor is orlistat;

(c) the sulfonyl urea is selected from the group consisting of acetohexamide, chlorpropamide, tolbutamide, tolazamide, gliclazide, glyburide or glibenclamide, glipizide, glimepiride, and gliquidone;

(d) the meglitinide is selected from the group consisting of mitiglinide, nateglinide, and repaglinide;

(e) the biguanide is selected from the group consisting of metformin, phenformin, and buformin;

(f) the thiazolidinedione is selected from the group consisting of rosiglitazone, pioglitazone, troglitazone, and tesaglitazar;

(g) the incretin mimetic is selected from the group consisting of exenatide, exedin-4 or AC2993; liraglutide, NN2211, or NNC 90-1170;

(h) the DPP-IV inhibitor is selected from the group consisting of sitagliptin and vildagliptin; and (i) the SGLT2 inhibitor is selected from the group consisting of dapaglifozin.

12. A method of treating or ameliorating type II diabetes in a subject, the method comprising administering to the subject a therapeutically effective amount of the compound of claim 1, or a salt, solvate, stereoisomer, geometric isomer, or tautomer thereof.

13. The method of claim 12, wherein the compound is administered as a pharmaceutical composition to the subject.

14. The method of claim 12, wherein the subject is further administered at least one additional agent useful for treating or ameliorating type II diabetes.

15. The method of claim 12, wherein the at least one additional agent is selected from the group consisting of α-glucosidase inhibitor, lipase inhibitor, sulfonyl urea, meglitinide, biguanide, thiazolidinedione, pramlintide, incretin mimetic, DPP-IV inhibitor, and SGLT2 inhibitor.

16. The method of claim 14, wherein at least one of the following applies:

(a) administering the compound to the subject allows for administering a lower dose of the at least one additional agent as compared to the dose of the additional agent alone that is required to achieve similar results in treating or ameliorating type II diabetes;

(b) administering the compound to the subject enhances activity, or reduces at least one side effect, of the at least one additional agent;

(c) the compound and the at least one additional agent are co-administered to the subject;

(d) the compound and the at least one additional agent are co-formulated.

* * * * *